United States Patent [19]

Lagow et al.

[11] 4,113,435
[45] Sep. 12, 1978

[54] CRYOGENICALLY CONTROLLED DIRECT FLUORINATION APPARATUS

[75] Inventors: Richard J. Lagow, Manchester; James L. Adcock; Norma J. Maraschin, both of Cambridge, all of Mass.

[73] Assignee: Massachusetts Institute of Technology, Cambridge, Mass.

[21] Appl. No.: 379,876

[22] Filed: Jul. 16, 1973

[51] Int. Cl.$^2$ .............................. B01J 1/00; B01J 8/02; C07C 53/16; C07C 121/00
[52] U.S. Cl. ..................................... 422/191; 165/63; 260/340.6; 260/465.7; 260/593 H; 260/614 F; 260/615 F; 260/648 F; 260/653; 260/694; 560/227; 562/605; 562/507; 562/583; 422/193; 422/198; 422/202
[58] Field of Search ................ 23/288 K, 288 H, 283, 23/260, 263, 252 R, 288 L, 288 M; 62/514, 555; 165/63

[56] References Cited

U.S. PATENT DOCUMENTS

| | | | |
|---|---|---|---|
| 1,929,665 | 10/1933 | Wilcox | 23/288 K |
| 2,418,797 | 4/1947 | Voorhees | 23/288 L X |
| 2,532,756 | 12/1950 | Brunjes et al. | 23/288 M |
| 3,305,000 | 2/1967 | Bullen et al. | 62/514 X |
| 3,409,408 | 11/1968 | Ballestra | 23/283 |
| 3,738,815 | 6/1973 | Pawloski et al. | 23/260 |
| 3,758,450 | 9/1973 | Margrave et al. | 260/94.9 H |

OTHER PUBLICATIONS

Kirk–Othmer Encyclopedia of Chemical Technology, 2nd ed., vol. 6, p. 471, (1965).

*Primary Examiner*—Joseph Scovronek
*Attorney, Agent, or Firm*—Arthur A. Smith, Jr.; David E. Brook

[57] ABSTRACT

An apparatus and process useful in direct fluorination of a variety of compositions, as well as the fluorinated compositions themselves. The apparatus comprises a cryogenic zone reactor, such as a packed column reactor, divided into a plurality of independently controllable cryogenic temperature zones. Means are also provided to introduce a reactant to be fluorinated as well as to introduce a mixture of fluorine gas and an inert gas. The direct fluorination process is carried out in the reactor as described above. At least the first zone of the reactor is chilled to a temperature below the freezing point of the reactant to be fluorinated. The reactant is then introduced into the reactor wherein it condenses upon a suitably provided fluorination surface, such as copper column packings. A mixture of fluorine gas and an inert gas, with the fluorine gas initially comprising a very small percentage of the mixture, but gradually increasing as fluorination proceeds, is then introduced into the reactor. After some degree of fluorination has been achieved in the first zone, it is allowed to warm whereas other zones in the reactor are cooled. The resulting temperature gradients cause the partially fluorinated materials to volatilize and move along the column. As the volatilized, partially fluorinated materials enter the subsequent chilled zone, they condense on a fresh fluorination surface and are further fluorinated. The temperature gradients are repeated as necessary to achieve the degree of fluorination desired. New fluorinated compounds are also disclosed. These include: perfluoro-2-methoxyethyl ether; perfluoro-1,4-dioxane; perfluoro-2,5-diketohexane; perfluorohexamethylethane; and monohydropentadecafluoroadamantane. Additionally, new syntheses for trifluoroacetic acid are disclosed. One synthesis comprises producing perfluoroethyl acetate by direct fluorination using a cryogenic zoner reactor, followed by hydrolysis of perfluoroethyl acetate. A second synthesis comprises fluorinating an acyl chloride followed by hydrolysis of the resulting acyl fluoride.

14 Claims, 3 Drawing Figures

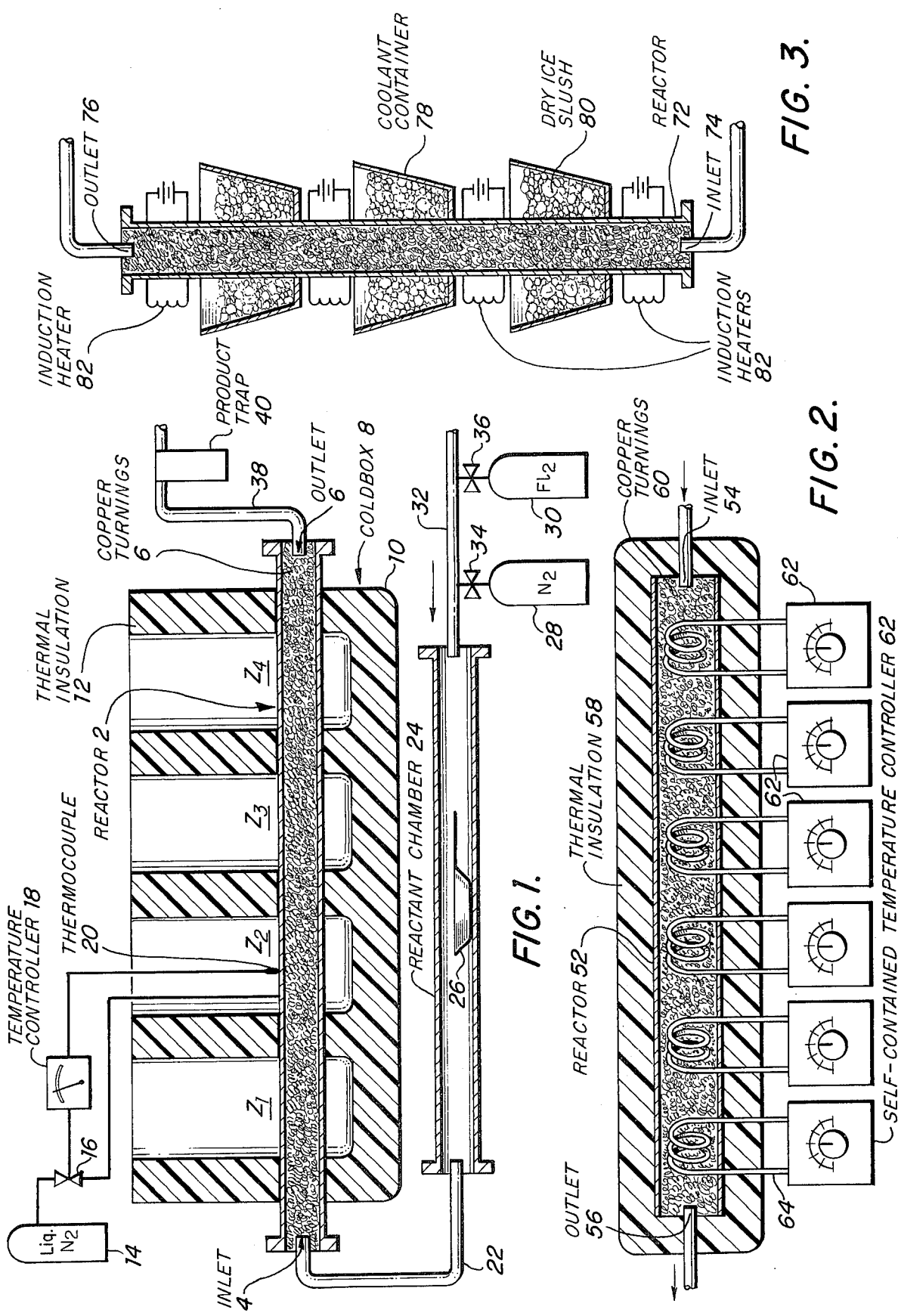

CRYOGENICALLY CONTROLLED DIRECT FLUORINATION APPARATUS

The invention described herein was made in the course of or under grants and/or contracts from the National Science Foundation and the U.S. Air Force.

BACKGROUND OF THE INVENTION

1. Field of the Invention

This invention is in the field of fluorine chemistry, and more particularly in the field of direct fluorination.

2. Description of the Prior Art

Fluorinated compositions are known to possess many outstanding properties. The range of these properties is indicated by the broad range of utilities for fluorinated compositions, which includes lubricants, heat transfer media, solvents, plasticisers, waxes, sealing liquids, refrigerants, surface active agents, oil and water repelling agents, inert solvents, diluents, monomers for preparing valuable fluoropolymers, and many others. Because of their value, extensive research has been devoted to preparing fluorinated products.

Fluorination processes present many problems, however. Whereas many compositions can be directly chlorinated or brominated, it has been recognized that fluorine is dissimilar to these halogens in regard to direct halogenation. See McBee et al., U.S. Pat. No. 2,533,132 and U.S. Pat. No. 2,614,129. In fact, even though direct fluorination of compositions with fluorine gas is a highly desirable process, prior attempts to use direct fluorination have usually produced low to mediocre yields. Additionally, the yields decrease as the molecular complexity of the reactants becomes greater.

Direct fluorination reactions involving elemental fluorine are characterized by quick evolution of large quantities of heat, ignition and flaming which promote product decomposition, often with explosive violence. In fact, it has been stated that "The fluorination process using elemental fluorine is one in which complete combustion of the hydrocarbon to carbon tetrafluoride and hydrogen fluoride is normally competing at a substantial rate with the desired fluorination." See Benning, U.S. Pat. No. 2,505,877. Thus, inability to control direct fluorination reactions to produce high yields of the desired fluorinated reactant without concomitant fragmentation of the desired product has prevented direct fluorination from becoming a widely accepted method of fluorination.

Because of the problems associated with previous attempts to use direct fluorination processes, a very diversified art has been developed to circumvent or obviate these problems utilizing inorganic, metallic fluorides, hydrogen fluoride, or electrolytic cells where no free fluorine is produced. The patent literature is replete with descriptions of such processes. A sampling includes: fluidized bed reaction employing metal fluorides such as cobalt trifluoride (McCleary, U.S. Pat. No. 2,795,026); syntheses of liquid fluorohalocarbons by reacting elemental fluorine with a fluidized mass of finely divided carbon particles in a reaction zone at 500°–800° F. and in the presence of chlorine or bromine (Mantell et al., U.S. Pat. No. 2,774,797); catalytic reaction of organic perchlorofluorocarbons with elemental fluorine or chlorine trifluoride in the presence of aluminum trifluoride catalysts (Tyczkowski et al., U.S. Pat. No. 2,831,;035); contacting vapor phase hydrocarbons which contain halogens other than fluorine with chlorine trifluoride or chlorine monofluoride (Muray, U.S. Pat. No. 3,099,695); contacting gaseous fluorine in the presence of alkali metal fluoride catalysts such as lithium fluoride at temperatures from −100° C. to 200° C. (Siegart, U.S. Pat. No. 3,480,667); and, combination electrochemical and chemical fluorination together with proper fractionation steps to fluorinate compounds containing chlorine or bromine using hydrogen fluoride, elemental fluorine or chlorine trifluoride (Fox, U.S. Pat. No. 3,709,800). It should be understood that the preceding fluorination processes are merely selected randomly from the patent literature, and are not intended to be inclusive of the general state of the art.

Recently, a new process for direct fluorination, known as the La-Mar process, has been used to fluorinate hydrogen-containing organic, organometallic and inorganic materials including aromatic ring systems. In this process, the hydrogen-containing material is placed in an enclosed chamber and an inert atmosphere such as nitrogen is introduced. Fluorine gas or an inorganic fluoride is introduced into the inert atmosphere in a very low initial concentration such as not to exceed about 6% at the end of 30 minutes. The temperature is maintained at a uniform low temperature so as to avoid uncontrolled fluorination. The La-Mar direct fluorination process is further disclosed in the following references: Lagow, R. J. and Margrave, J. L.; "Direct Fluorination of Organic and Inorganic Substances," Proc. Natl. Acad. Sci., 67; 4, 8A (1970); Lagow, R. J. and Margrave, J. L.; "The Reaction of Polynuclear Hydrocarbons with Elemental Fluorine," J. Am. Chem. Soc. (submitted); Lagow, R. J. and Margrave, J. L.; Chem. Eng. News, 48; 40 (January 12, 1970); and U.S. Patent Applications Ser. No. 718,128 (1968), abandoned Ser. No. 133,804 (1971), abandoned Ser. No. 133,803 (1971), and Ser. No. 133,865 (1971), now U.S. Pat. No. 3,750,450, issued Sept. 11, 1973 now U.S. Pat. No. 3,775,489, issued Nov. 27, 1973.

Although the La-Mar direct fluorination process has extended the application of direct fluorination, this process still has inherent limitations. For example, it is not suitable for for fluorinating many gases and liquids. Additionally, hydrocarbons containing oxygen are difficult or impossible to fluorinate in a controllable manner by the La-Mar process. One reason for this is, of course, that oxygen-containing compounds tend to fragment during fluorination resulting in the formation of free radicals which tend to initiate polymerization of reactants into polymers. It will be recognized, of course, that many valuable organic compounds contain functional groups including oxygen, such as ethers, esters, ketones, alcohols, carboxylic acids, etc. Thus, there still exists a need for a new direct fluorination apparatus and process which would provide sufficient flexibility to make it applicable to a wide range of reactants to be fluorinated, including oxygen-containing compounds.

SUMMARY OF THE INVENTION

In one embodiment, the invention relates to a new apparatus and process which are useful in direct fluorination of a variety of compounds.

The apparatus can be referred to as a cryogenic zone reactor. As this infers, the reactor is divided into a plurality of independently controllable cryogenic temperature zones. The reactor may be, for example, a horizontal or vertical cylindrical column which is packed wth copper turnings or other suitable fluorination packing.

The column reactor is divided by thermal insulation into a plurality of reaction zones, and each zone is provided with cooling means to provide a cryogenic temperature capability during fluorination.

The direct fluorination process is carried out in a cryogenic zone reactor. At least the first zone of the reactor is cooled to a temperature below the freezing point of the reactant to be fluorinated. When the reactant enters the first zone, it condenses upon a suitable fluorination surface such as the copper packings. Fluorine gas is introduced into the first zone in a fairly dilute mixture of fluorine and an inert gas. As fluorination proceeds, the concentration of fluorine gas is increased. After some degree of fluorination has been achieved in the first zone, it is warmed to volatilize the partially fluorinated reactants, whereas subsequent zones are simultaneously cooled below the freezing point of these materials. Thus, the partially fluorinated reactants are caused to move along the column and condense in another zone where further fluorination takes place on a fresh fluorination surface. These temperature cycles are repeated as necessary to produce the degree of fluorination desired, which is often perfluorination.

It can be appreciated, therefore, that considerations of kinetic and thermodynamic parameters lead to the cryogenic zone reactor and direct fluorination process described above. For a given system, there exists a cryogenic temperature where fluorine will not react with a delicate organic or inorganic reactant based upon kinetic and thermodynamic limitations. Above that temperature, however, there is a region in which the reaction rate may be controlled by carefully controlling the temperature. This results in the ability to use pure fluorine at one atmosphere of pressure in a direct fluorination which is controlled solely by temperature regulation.

The reactor and process described herein provide exceptional control over a direct fluorination reaction. Because of the low temperatures used, and because of the temperature cyclings to control the speed with which the partially fluorinated products pass through the reactor, exceptional yields are achieved. Product fragmentation, normally a problem with direct fluorination processes, is significantly reduced.

A number of secondary advantages are also inherent. Since the reactions are carried out at very low temperatures, corrosion of equipment, normally a problem with the high temperatures customarily used in fluorination reactions, is reduced dramatically. Also, the system is very clean in the sense that only the reactant to be fluorinated and elemental fluorine are required; thus, extraneous reactants, particularly other halogens, can be avoided.

The most important advantage is that the reactor and process described herein provide the capability of extending direct fluorination to the synthesis of compositions which heretofore could not be directly fluorinated. In fact, new fluorinated compositions have been produced which were previously impossible to produce by any fluorination technique; many of these are oxygen-containing compounds, which have traditionally been difficult to fluorinate. Some of the new compositions include: perfluoro-2-methoxyethyl ether; perfluoro-1,4-dioxane; perfluoro-2,5-diketohexane; perfluorohexamethylethane; and monohydropentadecafluoroadamantane. Additionally, the production of some perfluorinated compositions in significant yields open new syntheses to commercially important chemicals; an example is the synthesis of trifluoroacetic acid by hydrolyzing perfluorinated esters or acyl halides, the latter products being produced by the direct fluorination techniques and apparatus described herein.

BRIEF DESCRIPTION OF THE DRAWINGS

FIG. 1 illustrates, in schematic form, a horizontal cryogenic zone reactor of this invention having four independently controllable temperature zones;

FIG. 2 illustrates, in schematic form, an alternative embodiment of a horizontal cryogenic zone reactor of this invention which has six independently controllable temperature zones, each of which is controlled by a self-contained temperature controller;

FIG. 3 illustrates a vertical cryogenic zone reactor of this invention which is suitable for refluxing reactants.

DESCRIPTION OF THE PREFERRED EMBODIMENTS

The cryogenic zone reactor can be described in more detail by referring to the Figures. FIG. 1 illustrates schematically a horizontal cryogenic zone reactor. Reactor 2 is formed from a cylindrical horizontal column, the walls of which are fabricated from an inert material such as nickel. Other metals which are inert to fluorine can be used, and even glass can be used if replaced at reasonable times and if an extra separation step is not objectionable. The extra precautions with glass are necessary since the glass is slowly etched during the synthesis, probably due to the formation of some hydrofluoric acid, and because silicon tetrafluoride is also produced. Column 2 has an inlet 4, where the reactants are introduced to the column, and an outlet 6 is provided at the opposite end to allow fluorinated products and excess reactants to exit.

Column 2 contains an inert packing, such as copper turnings 6. In general, the column packing is chosen to provide a large surface area upon which the reactants can be deposited for reaction, to provide a catalytic effect, if possible, and is also chosen to be a good thermal conductor so that the packing can serve as a heat sink. The surface of the packing can be fluorinated, if desired. Examples of packings which are suitable for direct fluorination include copper turnings, copper cuttings, copper tacks, copper spheres, nickel turnings, etc. The preferred packing is small diameter fluorinated metal turnings, because they provide maximum surface area upon which the fluorine can attack reactant. Those skilled in the art will know, or be able to ascertain using no more than routine experimentation, many other suitable column packings.

Reactor 2 is contained in a cold box 8, which has outer walls 10 formed from a structural building material such as stainless steel. Thermal insulation 12, such as polyurethane foam or styrofoam, lines the inside walls of cold box 8 and surrounds column reactor 2 in sufficient thickness to provide four independently controllable cryogenic temperature zones $Z_1$, $Z_2$, $Z_3$ and $Z_4$. It is clear, of course, that more or less independently controllable temperature zones can be used, depending upon the requirements of the specific fluorination reaction employed.

Cryogenic temperatures can be maintained in each zone by suitable cooling means. For example, a source of liquid nitrogen 14 can be used to provide temperatures in the range of about $-60°$ C. to about $-196°$ C. Liquid nitrogen is fed separately into each zone through a control valve 16 which can be regulated by temperature controller 18 connected to a sensing means such as thermocouple 20. For purposes of simplification, the cooling means has been illustrated as being connected only to zone $Z_2$ of the reactor; it should be understood, of course, that usually each zone has its own set of temperature sensing and controlling means.

Reactants are fed to column reactor 2 through inlet line 22 which can be, for example, copper tubing. Inlet line 22 connects the inlet 4 of column reactor 2 with reactant chamber 24 which includes a vessel 26 to contain reactants which are to be fluorinated. Sources of nitrogen gas 28 and fluorine gas 30 are connected to reactant chamber 24 by tubing 32, and the flow of each is respectively controlled by valves 34 and 36. The nitrogen gas serves as an inert diluent, and other gases such as helium could be used, of course.

Fluorinated products and excess reactants exit from the reactor through outlet 6 which is connected by tubing 38 to a suitable trap 40, designed to collect the various components. Suitable traps might include, for example, one or more of an HF trap containing sodium fluoride pellets, a liquid nitrogen U-trap, a 78° C. glass trap, alumina trap to catch excess fluorine, etc.

The cryogenic zone reactor illustrated functions as follows. Reactants to be fluorinated are placed in vessel 26, and at least zone $Z_1$ is cooled to a temperature low enough to condense the reactants. The reactant in vessel 26 is vaporized and introduced into zone $Z_1$ where it condenses on copper turnings 6. A flow of nitrogen can be used to purge the reactor prior to introduction of the reactant, and the nitrogen also serves to carry vaporized reactant into column 2. Fluorine gas is then introduced by opening valve 36. The initial flow of fluorine is kept low so that it forms a very low concentration of total gas fed to the reactor; the concentration is raised as fluorination proceeds. In general, amounts of fluorine consistent with the La-Mar direct fluorination process are used. The exact concentration and amounts of fluorine gas or other fluorinating agent used will, of course, depend on the particular fluorination desired. Those skilled in the art can determine this using no more than routine experimentation. Zone $Z_1$ is allowed to warm, and zone $Z_2$ is cooled to move the reactants and partially fluorinated materials along the tube. Generally, although not always, the reactants become more volatile as they are fluorinated. This temperature sequencing is repeated for other zones as desired and until the amount of fluorination desired has been achieved.

The low temperatures aid in preventing fragmentation of delicate species and a new surface for fluorination is continually produced as the temperature changes in the various zones cause material to move along the reactor. It will be recognized that the optimum temperature-time conditions in each zone, and the number of zones required to obtain high yields are very much dependent on the relationship between volatilities of starting materials, the partially fluorinated intermediates and the fluorinated products as well as the resistance of a given material to fragmentation during fluorination. An optimized procedure for any specific fluorination will undoubtedly involve a number of different temperature cyclings during the reaction. Those skilled in the art will be able to ascertain these using the teachings presented herein together with no more than routine experimentation.

FIG. 2 illustrates an alternative horizontal packed column reactor. A horizontal column reactor 52 is provided with a reactant inlet 54 and a product outlet 56. Column reactor 52 is surrounded on all sides and ends by suitable thermal insulation 58. Copper turnings 60, or other suitable column packing, is closely packed inside reactor 52.

Extremely good temperature control is obtained in six independent zones by the use of six self-contained temperature controllers 62. These can be, for example, Freon controllers which are marketed by the Linde Division of Union Carbide. Each Freon temperature controller can be individually set to provide any desired cryogenic temperature in the range of from about −60° C. to +20° C. The desired temperature is maintained by circulating just enough Freon through the cooling coils 64 to remove excess heat present initially or generated in the highly exothermic fluorination reaction. The reaction of FIG. 2 is operated in a manner similar to that described supra and illustrated in FIG. 1.

FIG. 3 illustrates schematically a vertical embodiment of the cryogenic zone reactor described herein. Column reactor 72 is provided with an inlet 74 and an outlet 76. As in the horizontal embodiments, column 72 is suitably packed; a particularly effective packing for this embodiment consists of copper cuttings in the lower portion of the reactor and loosely packed copper turnings in the upper portion. The temperature is maintained in each distinct zone by filling coolant containers 78 with a suitable cooling medium such as a dry ice slush 80. The temperature of each zone is lowered by adding more or less of the cooling medium. The temperature can be raised quickly by a heating means, such as induction heating coils 82. Resistance heaters, or other suitable heating means could, of course, be used.

Vertical cryogenic zone reactors, of the type illustrated in FIG. 3, maximize reactant surface area available for fluorine attack, particularly when the reactant to be fluorinated tends to become a syrupy liquid during fluorination. Such liquids distribute themselves over the column packing by gravity flow, thereby increasing the surface area available for fluorine attack.

An additional feature of vertical embodiments is that they provide refluxing capability. If the upper portion is maintained at a temperature below the condensation point while the lower portion is held above a temperature at which it volatilizes, the gas flow entering from the bottom causes the volatile materials to be refluxed (i.e. cyclic vaporization and condensation) until a degree of fluorination or fragmentation is reached so that the volatiles may escape from the upper portion of the column and be collected or further fluorinated.

In operation, less volatile liquids flow by gravity counter to the gas flow, e.g. helium and fluorine. The fluorine gas serves to fluorinate the surface of the flowing liquid, and also strips the more volatile components from the liquid and carries them into the colder part of the vertical cryogenic zone reactor where they are condensed so that the process can be repeated.

As can be seen, the temperature of the various zones can be adjusted to establish a gradient for reflux of practically any volatilizable material. More zones allow more effective fractionation of the volatile components. It should also be understood that the reactants may be loaded into the column anywhere along the reactor gradient so that the less volatile liquids will not freeze and yet the uppermost zone can prevent losses of still more volatile products while the initial fluorination process can take place in the lower portions of the reactor which are adjusted at higher temperatures.

Although FIGS. 1 and 2 have illustrated horizontal packed columns, it should be understood that these columns could be used in a vertical manner. In fact, a combination horizontal and vertical reactor can also be formed by connecting columns of FIGS. 1 or 2 with that of FIG. 3. Also, the reactors can be used in other positions other than pure vertical or pure horizontal, if desired.

The cryogenic reactor and processes described herein can be used in direct fluorination of a large variety of compounds. They have particular advantage in fluorinating volatile solids, gases and liquids. Chemically, compositions which can be directly fluorinated include inorganic compounds; acyclic or cyclic, saturated or unsaturated, substituted or unsubstituted aliphatics; substituted or unsubstituted aromatics; heterocyclics; and polymeric materials.

The extraordinary capability of the reactor and process in fluorinating a wide variety of compounds is indicated by the fact that organic compounds having functional groups such as ethers, esters, ketones, carboxylic acids, nitriles, alcohols, aldehydes, amines, imines, sulfides, sulfates, carbonates, nitro, nitriles, etc., and even combinations of these functionalities, can be fluorinated successfully. Many of these, particularly those containing oxygen, were difficult or impossible to fluorinate using direct fluorination techniques or other processes and apparatus heretofore known.

The synthesis of perfluorinated ethers using heretofore known technology, for example, was difficult or impossible to accomplish. See, for example, Drake et al., U.S. 3,125,581; Watson, U.S. Pat. No. 3,291,884; Lorenz, U.S. Pat. No. 3,321,532; Litt et al., U.S. Pat. No. 3,453,333; 3,291,844; and Litt et al., U.S. Pat. No. 3,542,859. Two ethers which can be successfully fluorinated with the cryogenic zone reactor described herein are glyme (1,2-dimethoxyethane) and diglyme (bis(2-methoxyethyl)ether). These ethers have not been previously commercially available, and direct fluorination of these can be extrapolated to lower molecular weight ethers which tend to be easier synthetic targets. Simply illustrated, these fluorination reactions are:

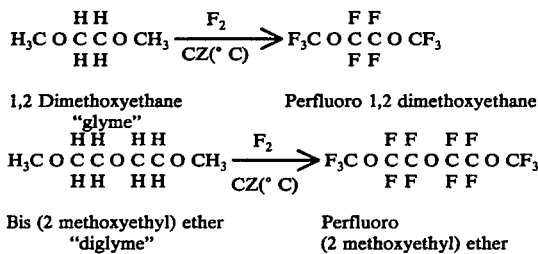

1,2 Dimethoxyethane "glyme"     Perfluoro 1,2 dimethoxyethane

Bis (2 methoxyethyl) ether "diglyme"     Perfluoro (2 methoxyethyl) ether

The symbol "CZ(°C)" is used to indicate that these reactions are carried out with cryogenic zone control of temperatures using the apparatus and processes described herein. Typical syntheses for perfluoroglyme and perfluorodiglyme, together with product characterization data for the products, are given infra in Examples 1 and 2.

Another ether which can be successfully perfluorinated is the cyclic ether dioxane. Although attempts have been made to fluorinate dioxane by prior art techniques, such as with electrochemical cell technology, these attempts have resulted in very small yields (e.g. 4%) of fragmentation products such as perfluoro-1,2-dimethoxyethane, without any evidence of the presence of the perfluorinated dioxane. The cryogenic zone reactor of this invention can be used to synthesize perfluorodioxane in fairly high yields (e.g. 39%). This synthesis is simply illustrated as follows:

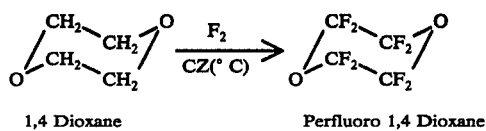

1,4 Dioxane     Perfluoro 1,4 Dioxane

A typical synthesis for perfluoro-1,4-dioxane, together with product characterization data, is given in detail infra in Example 3.

Perfluoro esters have been shown only recently to exist as stable compounds. See Varetti, E. L. and Aymonino, P. J., J. Molecular Structure, 7, p. 135 (1971); and, DeMarco, R. A., Couch, D. A. and Shreeve, J. P.; J. Org. Chem., 37, p. 3332 (1972). The sensitivity of the ester linkage to attack and hydrolysis by acids has precluded their synthesis in hydrogen fluoride electrochemical cells. Other methods of fluorination have also proved unsuccessful in producing perfluoro esters. On the other hand, the apparatus and processes described herein provide the capability to successfully fluorinate esters.

One ester which can be successfully perfluorinated is ethyl acetate. This synthesis can be illustrated simply as follows:

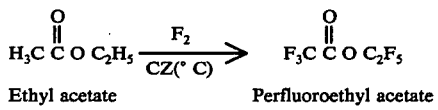

Ethyl acetate     Perfluoroethyl acetate

A typical synthesis for perfluoroethyl acetate, together with product characterization, is described in detail infra in Example 4.

Perfluoroethyl acetate can be hydrolyzed to yield two moles of trifluoroacetic acid, a known and commercially significant bulk chemical. Simply illustrated, the reaction is as follows:

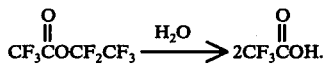

The perfluoroethyl acetate is exceptionally hydrolytically unstable, and virtually any aqueous conditions are satisfactory for forming the trifluoroacetic acid. Thus, neutral, acidic or alkaline aqueous solutions are satisfactory, as are any temperatures between the freezing point and boiling point of the solution.

The commercial significance of trifluoroacetic acid, as well as prior art hydrolysis of trifluoroacetyl fluoride and trifluoroacetyl chloride to produce it, are described in Bruce, U.S. Pat. No. 2,922,816 and Nychka, U.S. Pat. No. 3,288,850, the teachings of which are hereby incorporated by reference.

Perfluoro ketones can also be synthetically produced using the cryogenic zone reaction described herein. This is a particularly significant achievement in view of the prior art's almost unanimous conclusion that acetones were exceptionally difficult or impossible to perfluorinate by direct fluorination techniques. U.S. Pat. No,. 3,379,765. to Anello et al., for example, states, "Fluorination, and particularly perfluorination of ketones, however, has posed special problems due to the well known tendency of these materials to dissociate and form a variety of decomposition products under fluorinating conditions." Additionally, it has been stated that no practical synthesis of perfluoroketones was available. See Lovelace, Rausch and Postelnek, *Aliphatic Fluorine Compounds*, Reinhold Publishing Corp., N.Y., 1958, pp. 181–187; and, Fawcett et al., U.S. Pat. No. 3,185,735. Other patentees have simply stated, "Disadvantages entailed in use of hazardous elemental fluorine are obvious." See Nychka et al., U.S. Pat. No. 3,164,637 and Anello et al., U.S. Pat. No. 3,257,457.

The perfluorination of 2,5-diketohexane, by the techniques described herein, results in its perfluoro analogue. This fluorination is simply illustrated as follows:

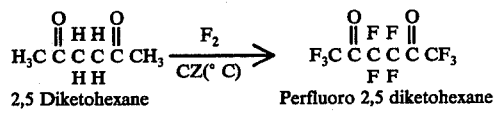

2,5 Diketohexane      Perfluoro 2,5 diketohexane

A typical synthesis of perfluoro-2,5-diketohexane is given in detail infra in Example 5.

Some alkanes are also difficult to fluorinate, and an example of such an alkane is neopentane. Fluorine chemists have directed considerable efforts towards fluorinating neopentane, without much success. This symmetrical, highly branched hydrocarbon has been found to be very difficult to fluorinate because it is sterically crowded and vibrational relaxation of the energy released is hindered.

In fact, traditional fluorination processes such as with cobalt trifluoride or fluorine gas have not been satisfactory for producing perfluoroneopentane. See Barber, E. J., Burger, L. L., and Cady, G. H.; J.Am.Chem.Soc., 73; 4241 (1951); and Maxville, A. F., Detoro, F. E., Bigelow, L. A.; J.Am.Chem.Soc. 82; 5827 (1960). Perfluoroneopentane has been formed, however, in a mixture of perfluoropentanes prepared by Dresdner, R. D.; J.Am.Chem.Soc., 77; 6633 (1955).

Perfluoroneopentane is of special interest because it possesses high symmetry. It is perhaps the most nearly spherical molecule known and its exterior surface is almost entirely fluorine bound to carbon. Unusual physical properties might be expected from interaction of the projecting non-bonding electrons and from the inert nature of the surface.

Perfluoroneopentane can be synthesized using the cryogenic zone reactor and the methods described herein. This new synthesis has the advantages of higher yields and hydrocarbon starting materials. The reaction can be illustrated as follows:

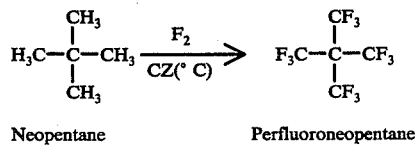

Neopentane      Perfluoroneopentane

A typical synthesis for perfluoroneopentane, together with product characterization, is given in detail infra in Example 6.

Another alkane which has proven to be more difficult to fluorinate than neopentane is hexamethylethane. This is a solid which is very volatile at room temperature. Perfluorohexamethylethane has not been previously reported, and it is known that highly branched hydrocarbons are among the most difficult types of compounds to fluorinate. See Barber, E. J., Burger, L. L. and Cady, G. H.; J. Am. Chem. Soc. 73, 4241 (1951); and Merrill, A. F., Detoro, F. F. and Bigelow, L. A.; J. Am. Chem. Soc., 82; 5827 (1960). Hexamethylethane can be fluorinated using the cryogenic zone reactor and methods described herein. Specific details of a typical synthesis are presented infra in Example 7, and the fluorination reaction can be illustrated simply as:

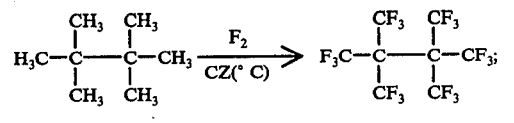

Hexamethylethane      Perfluorohexamethylethane

Direct fluorination of unusual hydrocarbon structures, which are difficult to fluorinate, can also be achieved using the cryogenic zone reactor and processes described herein. Thus, the direct fluorination of norbornadiene to produce perfluoronorbornane, norbornane to perfluoronorbornane, 1-methyladamantane to produce perfluoro-1-methyladamantane, and bicyclo(2,2,2)octane to its perfluorinated analogue can all be accomplished. Typical syntheses for these are described in greater detail infra in Examples 8–11, and these direct fluorination reactions can be simply illustrated as follows:

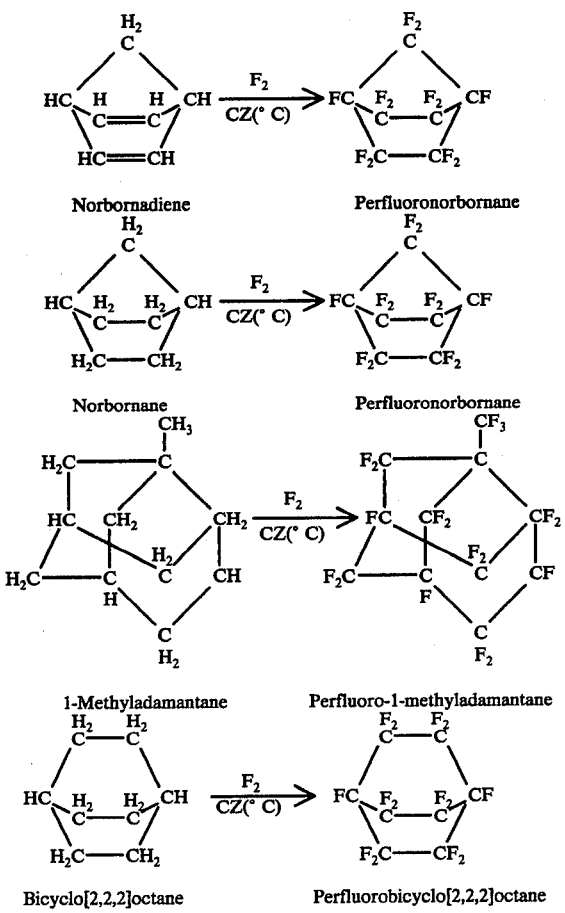

Norbornadiene      Perfluoronorbornane

Norbornane      Perfluoronorbornane

1-Methyladamantane      Perfluoro-1-methyladamantane

Bicyclo[2,2,2]octane      Perfluorobicyclo[2,2,2]octane

Fluorinated carboxylic acids have heretofore been prepared primarily by the electrolysis of hydrocarbon acids in the presence of hydrogen fluoride. See Bruce, U.S. Pat. No. 2,927,941. More recently, two new and more complex syntheses have been described in the patent literature. Thus, Pittman et al., in U.S. Pat. No. 3,409,647, describe a synthesis involving the reaction of a fluoroketone with an alkali metal fluoride to convert the carbonyl radical of the ketone into alkali metal fluorocarbinolate radical, which is then reacted with an ester of an omega haloaliphatic acid to yield a fluoroalkoxy aliphatic acid ester containing a fluorine on the alpha carbon atom of the alkoxy moiety. Thom, U.S. Pat. No. 3,723,485, describes the synthesis of perfluorocarboxylic acids by pyrolizing perfluoroalkanesulfonate salts of yttrium, scandium and rare earth elements in an inert atmosphere to provide carboxylic acids when hydrated salts are employed.

Perfluorocarboxylic acids can be prepared using the cryogenic zone reactor and processes described herein. Several alternative techniques can be used, including direct fluorination of the analogous acids or fluorination of compounds containing other functional groups, such as acid chlorides, with later hydrolysis to the acids. The latter technique is preferred.

One fluorinated carboxylic acid which can be prepared is perfluorocyclohexanoic acid. Simply illustrated, this synthesis is as follows:

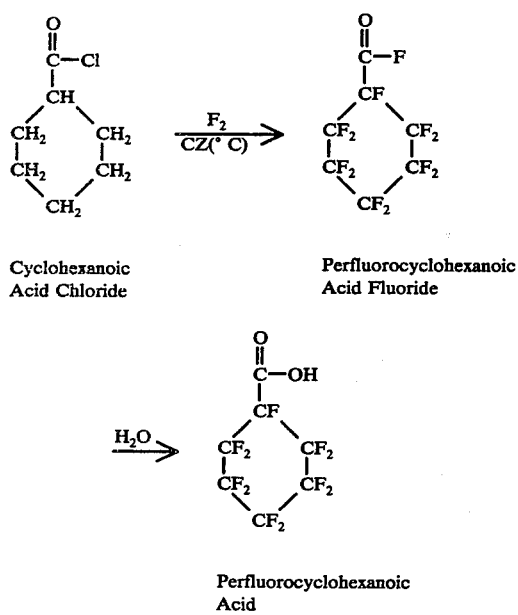

A typical synthesis of perfluorocyclohexanoic acid, together with characterization data for the products, is given in detail infra in Example 15.

Another carboxylic acid which can be produced by direct fluorination in a cryogenic zone reactor of this invention is tetrafluorooxadiacetic acid. This can be produced from two fluorinated materials, the first being perfluoro-N-fluoromorpholine and the second being perfluorodiglycolic acid fluoride. These reactions can be simply illustrated as follows:

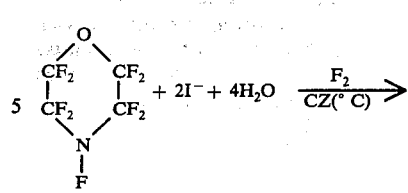

N-fluoromorpholine

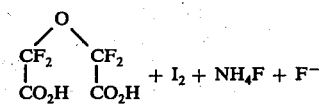

Tetrafluorooxadiacetic Acid

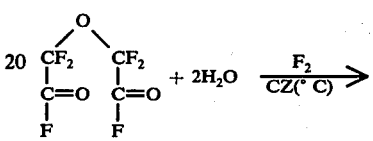

Diglycolic Acid Fluoride

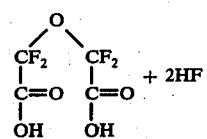

Tetrafluorooxadiacetic Acid

Typical synthesis of these two perfluorinated materials, together with characterization of products obtained, are presented in detail infra in Examples 13 and 14.

Nitriles, upon fluorination, yield N-fluoroamines which can be converted to acids by reaction with potassium iodide, or to nitriles by reaction with two moles of triphenylphosphine. In addition, N-fluoroperfluoroamines are stable and fairly inert substances which can be easily hydrolyzed after fluorination in order to remove any carbonyl containing species which can arrive either because of the presence of traces of water in the starting material or mainly becuase of cleavage at the C—O—C linkage in ethers.

One nitrile which can be fluorinated using the cryogenic zone reactor of this invention is glutaronitrile. This reaction is simply illustrated as follows:

Glutaronitrile    1,7-diazaperfluoroheptane

A typical direct fluorination of glutaronitrile, together with characterization data for the products obtained, is presented infra in detail in Example 16.

The above discussion illustrates only a small portion of compounds which can be fluorinated. Some others are further illustrated in the examples, but even these are not intended to be exclusive. Those skilled in the art will be able to fluorinate a great number of compositions using the apparatus and process described herein, using no more than routine experimentation to ascertain the appropriate reaction conditions for each synthesis.

Although the term "cryogenic" temperatures has been used, products can be fluorinated as described herein at temperatures not normally considered to be cryogenic. Thus, the term "cryogenic" is used to include temperatures at which reactants can be condensed in the various zones of the reactor; generally, these temperatures are in the range of about −190° C. to about +20° C. Below about −190° C., fluorination doesn't appear to take place in appreciable amounts.

It will be recognized by those skilled in the art that there are many modifications or equivalents to the equipment and processes specifically described herein. For example, cooling or heating means other than those specifically disclosed can be used. Additionally, other reactor constructions which are different but include a multiplicity of cryogenic, independently controllable temperature zones could also be used. In fact, it isn't necessary to have multiple zones if temperature cycling can be achieved by other means; multiple zones simply make it easier. Further, fluorinating agents other than elemental fluorine can be used, even though elemental fluorine is clearly preferred. For example, chlorine trifluoride or bromine trifluoride can be used if it is not objectionable to obtain products which are partially chlorinated and brominated. In fact, the cryogenic zone reactor itself might be used in other than fluorination reactions. Such modifications and equivalents are intended to be included in the claims presented herein.

The invention is further specifically illustrated by the following examples.

EXAMPLE 1

Cryogenic Zone Direct Fluorination of 1,2-dimethoxyethane

An apparatus as illustrated in FIG. 1 was used. Reactant chamber 24 was formed from nickel and was 18 inches long and had a width of 1.5 inches. Reactor 2 was 24 inches long, had an inside diameter of 1.0 inch, and was tightly packed with fluorinated copper turnings. Reactor 2 and reactant chamber 24 were connected to each other and to the sources of inert (helium) and fluorine gases by 0.25 inch copper tubing. Cold box 8 was made from stainless steel with an overall depth of 9 inches and a width of 6 inches. The individual temperature zones measured 4×4×8 inches and were insulated with polyurethane foam. Suitable traps were attached to the outlet from the cryogenic zone reactor.

4.015 g. (0.045 mol.) of 1,2-dimethoxyethane was placed in a nickel boat in the reactant chamber and evaporated employing a flow of 50 to 100 cc. helium into the reactor. All zones were cooled to −78° C., a temperature below the freezing point of the ether (−58° C.), with a dry ice alcohol mixture introduced into the four temperature zones. An initial flow of 0.5 cc./min. fluorine and 20 cc./min. helium was started. After 12 hours, the fluorine was increased to 1.0 cc./min. After an additional 12 hours, zone one was allowed to run out of dry ice. Twelve hours after zone one was clear of dry ice, the fluorine flow was increased to 1.5 cc./min. while still maintaining helium flow at 20 cc./min. The fluorine flow was maintained at 1.5 cc./min. On alternate days, the helium was reduced to 10 cc./min. followed by allowing one additional zone to clear of dry ice. Subsequent reductions to five, then to zero cc./min., followed each time by warming of one additional zone, which allowed renewal of the reactant surface inside the reactor. Finally, as the reactor warmed under a flow of pure fluorine, the fluorinated ether was passed through a metal trap filled with sodium fluoride pellets and into a glass trap maintained at −78° C. The raw fluorocarbon ether represented a raw yield of about 85% of the expected yield based on moles of the parent ether. This mixture contained several hydrofluoro ethers and other hydrolytically unstable and corrosive products along with a smaller amount of perfluorinated fragments. The yield of the hydrofluoro ethers in most cases exceeded the yield of perfluoroethers due to incomplete reaction. These products were removed by aqueous alkali hydrolysis and the hydrolytically stable ethers fractionated. The bulk of the desired products was collected in the −95° C. and −130° C. traps (combined weight 2.48 g., 20.6%). Final purification was accomplished using gas-liquid chromatography using a fluorosilicon (QF-1-0065, 13% on chromosorb P, 80/100 mesh) column. The perfluoroglyme had the following characteristics.

Perfluoro-1,2-Dimethoxyethane (perfluoroglyme): The product of the reaction of 1,2-dimethoxyethane with fluorine was a gas at room temperature (b.p. 16.7° C.). The molecular weight determined by the ideal gas method was 269 cf. 270 for $C_4F_{10}O_2$. The $^{19}F$ NMR consisted of a triplet at 59.54 ppm. and a quartet at +94.19 ppm. relative to $CFCl_3$[1] with coupling constant 9.2 hz. and relative intensities 3:2. The infrared spectrum exhibited bands at 1410(w), 1295(s), 1250(s), 1200(w), 1170(sh), 1155(s), 1105(w), 923(w), 887(m), 865(w), 819(w), 690(w) wavenumbers. The mass spectrum contained no parent peak but shows strong peaks at m/e 135 corresponding to the symmetrical cleavage of the molecule ($CF_3$-O-$CF_2$). Other strong peaks are m/e 119, $C_2F_5$; m/e 100, $C_2F_4$; m/e 69, $CF_3$; m/e 50, $CF_2$ and m/e 47, CFO. Elemental analysis yielded the following values: Calculated for $C_4F_{10}O_2$, %C 17.79, %F 70.36; Found %C 17.41, %F 70.08. The yield was 21%.

[1] NMR samples were condensed into capillary tubes, sealed, and immersed in a solution of $CFCl_3$ (30%) tetramethylsilane (5%) and carbon tetrachloride (65%) contained in a standard NMR tube.

If the products of the above reaction were not hydrolyzed, a second major product may be isolated which in some cases exceeds the amount of perfluoro-1,2-dimethoxyethane. This ether was a liquid with a disagreeable odor and may be quite toxic. Its molecular weight was determined to be 251 cf. 252 for $C_4HF_9O_2$. Its $^{19}F$ NMR spectrum exhibited a triplet at +59.22 ppm. and a quartet at +93.63 ppm. with a coupling constant of 9.4 hertz and a relative intensity of 3:2 respectively: a doublet centered at +88.36 (J=70.0 hz.) split into triplets (J=4.4 hz.) and a triplet at +92.47 ppm. (J=4.6 hz.) relative to $CFCl_3$ with relative integrals of 2:2. The proton NMR consisted of a triplet at −6.26 ppm. relative to TMS with coupling constant equal to 68.6 hz. in good agreement with the doublet splitting in the $^{19}F$ NMR. If the proton is irradiated the $^{19}F$ doublet decayed into a singlet. This information is consistent with a structure containing a proton in the alpha position. The mass spectrum supports this conclusion. The two peaks corresponding to "symmetrical" cleavage at m/e 135, $C_2F_5O$, and m/e 117, $C_2HF_4O$, are both strong with relative intensities of 1:1.5 respectively as are the very strong peaks at m/e 69, $CF_3$, and m/e 51, $CHF_2$, of relative intensities 1:1.5. Other, less intense peaks support this conclusion.

The infrared spectrum contains a weak proton absorption at 3028 cm$^{-1}$ in addition to carbon fluorine and carbon oxygen bands at: 1400(w,b), 1370(w), 1295(s), 1250(s), 1192(m), 1179(sh), 1159(s), 1125(s), 1040(m), 910(m), 853(w), 818(m), 700(w) cm$^{-1}$. The yield was about 25%.

It is believed that the yield of perfluoroglyme is not optimum, and could be improved by recycling any partially fluorinated material. Also a cryogenic zone reactor having temperature control beyond −78° C. might also greatly improve the yield.

EXAMPLE 2

Cryogenic Zone Direct Fluorination of bis(2-methoxyethyl)ether

The apparatus and procedure of the preceding Example were used except as follows. Bis(2-methoxyethyl) ether (1.79 g., .0134 mol.) was evaporated at 50° C. into the four zone cryogenic reactor (zone 1, −40° C., zones 2,3,4 at −78° C.) using a 80 to 100 cc./min. flow of helium gas. After six to eight hours the helium flow was reduced to 20 cc./min. and a 0.5 cc./min. flow of fluorine was started. A similar procedure to that used in Example 1 was used to complete the reaction. The raw products were fractionated through −63°, −78°, −95° and −196° C. traps. Perfluorobis(2-methoxyethyl) ether was collected from the −78° C. and −95° C. traps (yield 0.83 g., 16.1%).

Perfluorobis(2-methoxyethyl)ether: The product isolated from the reaction of bis(2-methoxyethyl)ether with elemental fluorine was a volatile liquid (b.p. 60°-63°C.). Its molecular weight was determined to be 385 cf. 386 for $C_6F_{14}O_3$. The $^{19}F$ NMR exhibits a triplet at +59.30 ppm. and a quartet at +92.84 ppm. (J=9.4 hz.) and a singlet at +91.61 ppm. relative to $CFCl_3$. The relative integrals of the absorptions are 3:2:2 respectively.

The infrared spectrum exhibits bands at: 1385(w), 1295(s), 1250(s), 1220(sh,w), 1200(w), 1165(s), 1145(s), 920(sh), 910(m), 770(m), 697(w), 681(sh), wavenumbers.

The mass spectrum exhibits strong peaks at m/e 185, $C_3F_7O$; m/e 135, $C_2F_5O$, m/e 119 $C_2F_5$, m/e 100 $C_2F_4$, m/e 69, $CF_3$ and m/e 50, $CF_2$. Elemental analysis yielded the following values: calculated for $C_6F_{14}O_3$ %C 18.67, %F 68.90; found %C 18.64 %F 69.94. The yield was 16%.

As in the preceding Example, it is believed that the yield of perfluorobis(2-methoxyethyl)ether was not optimum and could be improved as discussed in the preceding Example.

EXAMPLE 3

Cryogenic Zone Direct Fluorination of Perfluoro-1,4-dioxane

An apparatus as illustrated in FIG. 1 and as described in Example 1 was used.

A 2-gram sample of 1,4-dioxane was evaporated employing a flow of 50 to 100 cc. helium into a gradient reactor containing four distinct zones. By maintaining the first two zones at a temperature slightly below the freezing point of 1,4-dioxane most of the material was collected in these traps; zones three and four were kept colder to prevent losses. All zones were then cooled to a temperature 30° lower than the freezing point of the hydrocarbon by means of a cryogenic temperature controller (Cryogenic Controls, Burbank, California). An initial flow of 0.5 cc./min. fluorine and 20 cc./min. helium was started and after 12 hours zonme one was allowed to warm to a temperature sufficient to allow mass transfer. Twelve hours after the zone reached this temperature the fluorine was increased to 1.5 cc./min. while still maintaining helium flow at 20 cc./min. The fluorine flow was maintained at 1.5 cc./min. On alternate days the helium was reduced to 10 cc./min. followed by allowing one additional zone to warm. Subsequent reductions to five then zero cc./min. followed each time by warming of one additional zone allowed renewal of the reactant surface inside the reactor. Finally, as the final zone of the reactor warmed stepwise under a flow of pure fluorine the fluorinated compound passed through a metal trap filled with sodium fluoride pellets and into a glass trap maintained at −196°. The mixed fluorocarbons collected represented a mass yield of from 80% to 100% of the expected mass yield based on moles of the parent ether. This mixture contains many hydrofluoro species and other hydrolytically unstable and corrosive products along with some perfluorinated fragments. The yield of the hydrofluoro species in most cases exceeded the yield of perfluoro species due to incomplete reaction. In the case of dioxane these other products were removed by aqueous alkali hydrolysis and the hydrolytically stable ethers fractionated. Final purification was accomplished using gasliquid chromatography. The fluorinated dioxane had the following characteristics.

Perfluoro-1,4-Dioxane: The product of the reaction of 1,4-dioxane with fluorine is a gas at room temperature (b.p. 15.9° C.). The molecular weight determined by the ideal gas method was 232.7 cf. 232.0 for $C_4F_8O_2$. The $^{19}F$ NMR consisted of a singlet at $\phi$ + 90.78 ppm. (relative to $CFCl_3$, external). The infrared spectrum exhibits bands at: 1435 (w), 1369(w), 1311(sh), 1303(s), 1232(vs), 1163(sh), 1149(s), 1113(s), 890(m), 665(m) wave numbers. The mass spectrum shows no parent peak but shows a peak at m/e 213 corresponding to the molecular ion minus a fluorine $C_4F_7O_2$. Other strong peaks are m/e 119, $C_2F_5$; m/e 100, $C_2F_4$; m/e 69, $CF_3$; m/e 50, $CF_2$ and m/e 47, CFO. Elemental analysis yielded the following values: Calculated for $C_4F_8O_2$, %C 20.71, %F 65.50; Found %C 20.63, %F 65.67.

Other products from the dioxane fluorination included perfluoro-1,2-dimethoxy ethane (5%), perfluoro dimethyl ether (~10%) as well as many hydrofluoro dioxanes.

EXAMPLE 4

Cryogenic Zone Direct Fluorination of Perfluoro(ethyl acetate)

The apparatus and general procedure of the preceding Example were used except that ethyl acetate was substituted for the 1,4-dioxane. Ethyl acetate (1.74 g., 19.8 mmol) was evaporated into a four-zone gradient cryogenic reactor cooled to −100° C. using a 150 cc./min. flow of helium over a 12-hour period. A flow of 0.5 cc./min. fluorine and 20 cc./min. helium was started. After 12 hours, the fluorine flow was increased to 1.0 cc./min. In 12 hours, the fluorine was increased to 1.5 cc./min. and the helium flow was decreased to 10 cc./min. Zone 1 was allowed to warm to equilibrium while maintaining zone 2 at −100° C. After 24 hours, the helium was reduced to 5 cc./min. Zone 2 was allowed to warm to equilibrium while maintaining zone 3 at −100°C. After 12 hours, the helium was shut off. In 12 additional hours, zone 3 was allowed to warm and zone 4 was maintained at −100° C. After 12 hours, the fluorine was increased to 2.0 cc./min. After 24 hours, the temperature of zone 4 was raised to −90° C., and 24 hours later raised to −45° C. and then to room temperature under a flow of 2.0 cc./min. fluorine.

The system was purged with helium. The product from the reactor passed through a hydrogen fluoride trap filled with sodium fluoride pellets and then into a glass collection trap. This trap was sealed, removed from the system and the product fractionally vacuum distilled. The products isolated include: perfluoroethyl acetate (0.23 g., 5%); α-hydrotetrafluoroethoxy carbonyl fluoride (0.41 g., 12%),α-hydrotetrafluoroethyl trifluoroacetate (0.96 g., 23%) and trifluoroacetyl fluoride (25%).

The perfluoro(ethyl acetate) and other products obtained were characterized as follows.

Perfluoro(Ethyl Acetate): The infrared spectrum of perfluoro (ethyl acetate) in cm.$^{-1}$ is as follows: 1853(s) ($\nu$C=O), 1339(m), 1249(vs), 1222(s), 1203(s), 1179(ms), 1110(vs), 1090(s), 855 (w), 760(m), 740(sh), 705(w), 681(m), 530(w) (cm.$^{-1}$). The $^{19}$F NMR as a neat liquid relative to external CFCl$_3$ in carbon tetrachloride consists of a slightly broadened singlet at +79.89 ppm., a triplet at +90.02 ppm. and a quartet at +95.04 ppm. with coupling constant of 2.4 hertz. The relative integrals were 3:3:2 respectively. This data is rationalized below and compares well with that published by Shreeve, et al.

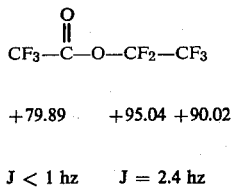

$$CF_3-\overset{\overset{O}{\|}}{C}-O-CF_2-CF_3$$

+79.89    +95.04 +90.02

J < 1 hz    J = 2.4 hz

Calculated for C$_4$O$_2$F$_8$ C20.7 O 13.8% F 65.5% Found C 20.59% O 13.76% F 65.3%.

Perfluoro(ethyl acetate) is a gas at room temperature.

α-hydrotetrafluoroethyl Trifluoroacetate: The major product isolated from the reaction of ethyl acetate and elemental fluorine is the trifluoroacetic acid ester of the unstable alcohol α hydro-tetrafluoroethyl alcohol. This product is a liquid (b.p. 30°–33° C.). This fluoro alcohol ester was identified by a molecular weight determination (214.2 cf. 214 for C$_4$F$_7$HO$_2$), infrared, $^{19}$F and H nuclear magnetic resonance. The infrared spectrum exhibits bands at: 3000(w), 1834(s), ($\nu$c=0), 1200 (vs), 1147(s), 1110(vs), 1070(m), 925(m), 835(w), 770(w), 704(m), 633(w).

The $^{19}$F NMR consists of a singlet at +78,8 ppm. a doublet ($j$=5.8hz) split into doublets ($j$=3.2 hz) at +87.2 ppm., and a doublet ($j$=49.9 hz) split into quartets ($j$=6.0 hz) at +153.8 ppm. relative to external CFCl$_3$/CCl$_4$. The $^1$H NMN is a doublet ($j$=50.3 hz) split into quartets ($j$=2.1 hz) at −6.0 ppm. relative to external TMS/CCl$_4$.

A major factor affecting yields in this reaction is presumed to be the fluoride ion catalyzed rearrangement of perfluoro(ethyl acetate) to two moles of trifluoroacetyl fluoride. Because sodium fluoride pellets are used to absorb the hydrogen fluoride liberated in the reaction of elemental fluorine with hydrogen substituents some of the perfluoroester is probably lost due to cleavage and rearrangement by sodium and/or hydrogen fluoride to trifluoroacetyl fluoride.

α-Hydrotetrafluoroethoxy Carbonyl Fluoride: This is a at room temperature. Its infrared carbonyl stretching frequency is at 1876 cm.$^{-1}$. The $^{19}$F NMR consists of a broad singlet at +22.9 ppm., a doublet ($j$=6 hz) split into doublets ($j$=3 hz) at +87.6 ppm., and a doublet ($j$=51 hz) split into quartets ($j$=6hz) at +153.5 ppm. relative to external CFCl$_3$/CCl$_4$. The $^1$H NMR is a doublet ($j$=51 hz) split into quartets ($j$=3 hz) at −5.85 ppm. relative to external TMS/CCl$_4$. The splitting is poorly resolved due to a small coupling from the aryl fluorine nucleus.

Trifluoroacetyl Fluoride: This is a gas identified by an infrared spectrum of an authentic sample.

Other products isolated in the reaction of ethyl acetate with elemental fluorine are listed as follows: CF$_4$, OCF$_2$, CF$_3$CFO, FCO$_2$CHFCF$_3$ and possibly FCO$_2$C$_2$F$_5$. The yield of CF$_3$CFO is quite variable (5 − 15%) from reaction to reaction.

The direct fluorination of ethyl acetate to the perfluorethyl and α-hydrotetrafluoroethyl esters of trifluoroacetic acid definitely indicate that this method has a unique advantage with respect to the fluorination of many classes of hydrocarbons.

EXAMPLE 5

Cryogenic Zone Direct Fluorination of 2,5-diketohexane

The apparatus and procedure of the preceding Example were used except that 2,5-diketohexane was substituted for the ethyl acetate. 2-5 diketohexane (1.74 g.)was evaporated into a four-zone gradient cryogenic reactor cooled to −100° C. using a 150 cc./min. flow of helium over a 12-hour period. A flow of 0.5 cc./min. fluorine and 20 cc./min. helium was started. After 12 hours, the fluorine flow was increased to 1.0 cc./min. In 12 hours, the fluorine was increased to 1.5 cc./min. and the helium flow was decreased to 10 cc./min. Zone 1 was allowed to warm to equilibrium while maintaining zone 2 at −100° C. After 24 hours, the helium was reduced to 5 cc./min. Zone 2 was allowed to warm to equilibrium while maintaining zone 3 at −100° C. After 12 hours, the helium was shut off. In 12 additional hours, zone 3 was allowed to warm and zone 4 was maintained at −100° C. After 12 hours, the fluorine was increased to 2.0 cc./min. After 24 hours, the temperature of zone 4 was raised to −90° C., and 24 hours later raised to −45° C. and then to room temperature under a flow of 2.0 cc./min. fluorine.

The system was purged with helium, and the product from the reactor passed through a hydrogen fluoride trap filled with sodium fluoride pellets and then into a glass collection trap.

It was purified by fractional distillation and gas chromatography to yield approximately 5% product. The perfluorinated product was characterized by its infrared spectrum which contained carbonyl bands at 1887 cm$^{-1}$ and 1830 cm$^{-1}$ and its characteristic carbon-fluorine activity. The molecular weight was determined to be 292, compared to a calculated value of 294.

EXAMPLE 6

Cryogenic Zone Direct Fluorination of Neopentane

The apparatus illustrated in FIG. 1 and described in Example 1 was used.

2.052 g. (2.82×10$^{-2}$ moles) of neopentane were condensed into the first two traps of the cold reactor, which had been flushed with helium and cooled to −78° C. The helium flow was initiated at 20 cc./min. and the fluorine flow at 1 ½ cc./min. and continued for 48 hours. The first trap of the cold reactor was allowed to warm and the third trap was cooled. The helium flow was shut off and 1 ½ cc./min. of pure fluorine passed through the system. Twenty-four hours later, the last trap was cooled to −78° C. and the second trap was warmed. A glass trap at the end of the system, filled with NaF, was also cooled to −78° C. After 24 hours, the third trap was warmed and following another 24 hours, the fluorine was shut off, a helium flow of 20 cc./min. was begun and the last trap of the cold reactor warmed. Helium was passed through the system for 12 hours after the last trap had reached room temperature. The glass trap was removed from the system, cooled in liquid nitrogen and evacuated. The trap was then allowed to warm to room temperature and was shaken periodically for 12 hours. The volatile material was pumped off into a liquid nitrogen cooled vial, diluted with CCl$_4$ and subsequently separated by gas chromatography. A 10, feet ¼ inch column of 10% SE-30 on Chromosorp P was held at 0° C. for the separation. Perfluoroneopentane has a retention time of 3.5 min. from injection. (0.849g.) (0.294×10$^{-2}$ moles) of perfluoroneopentane were obtained which corresponds to a 10.4% yield. The melting point was determined in a sealed capillary and found to be 72.5°-73° C. in agreement with the reported value. Anal: Calculated for C$_5$F$_{12}$: C, 20.84%; F, 79.15%; Found: C, 20.67%; F, 79.23%. The gas phase infrared spectrum contained three strong bands at 1300 cm$^{-1}$, 980 cm$^{-1}$ and 720 cm$^{-1}$ and a very weak band at 1190 cm$^{-1}$, in agreement with the reported spectrum. The F$^{19}$ NMR spectrum consisted of a singlet at −13.92 ppm. from an external trifluoroacetic acid reference. A value of −13.8 ppm has been reported for perfluoroneopentane. See Muller, N., Lauterbur, P. C., and Svatos, G. F.; J. Am. Chem. Soc., 79; 1801 (1957). The mass spectrum of the compound at 70 eV does not contain a parent peak, but exhibits a strong P-19 peak at 269. The CF$_3$$^+$ ion is the most intense peak in the spectrum. The known physical properties of this unusual, colorless, and extremely volatile fluorocarbon pose a very interesting problem. The intermolecular forces in fluorocarbons are not well understood; however, one would expect that any attraction would be due primarily to van der Waals interactions. The boiling points of the perfluoropentane isomers, n-perfluoropentane and iso-perfluoropentane, are known to be 29.3° C. and 29.9°-30.1° C. respectively. See Barber, E. J., Burger, L. L. and Cady, G. H.; J. Am. Chem. Soc. 73; 4241 (1951). In contrast, the melting point of perfluoroneopentane is 72.5°-73° C. Of course, the molecular weights are the same. One might expect that perfluoroneopentane would have a higher melting point than the other two isomers since it should exhibit more regular stacking in its crystalline form. However, one would predict that the normal and iso structures would have stronger van der Waals interactions. Unless the van der Waals interactions have a positive effect on volatility, this disparity in physical properties is striking. It has been observed that highly branched hydrocarbons often have higher melting and boiling points than linear isomers.

EXAMPLE 7

Cryogenic Zone Direct Fluorination of Hexamethylethane

The apparatus illustrated in FIG. 1 and described in Example 1 was used.

0.4237 g. (3.71 mmol) of hexamethylethane was placed in a nickel boat. The first two chambers of the cryogenic zone reactor were filled with Dry Ice-2-propanol slush (−78°). A glass trap at the end of the reactor was filled with approximately 1 g. of NaF and cooled to −78°. After flushing the system with helium, the flow was set at 20 cm.$^3$/min. and a fluorine flow of 1.5 cm.$^3$/min. was initiated. Fifteen hours later, the third compartments of the reactor was cooled and the first compartment allowed to warm to room temperature. Nine hours later, the helium flow was reduced to 8 cm.$^3$/min. After another 24 hours, the last compartment of the cold reactor was cooled and the second compartment allowed to warm to room temperature. The helium flow was also terminated at this time. Pure fluorine was allowed to run through the system for 32 hours. The fluorine flow was then terminated and a helium flow of 20 cm.$^3$/min. started. The last two compartments of the cold reactor were warmed to room temperature. The trap was removed, immersed in liquid nitrogen, and evacuated on a vacuum line. The trap was then warmed to room temperature, allowed to stand for 12 hours, and shaken periodically to allow the HF produced in the reaction to be absorbed by the NaF. The trap was reconnected to the vacuum line and the volatile products were trapped with liquid nitrogen. Mixed fluorocarbons (0.6461 g.) were obtained. This mixture was dissolved in CCl$_4$ and separated on a gas chromatograph at 20°. A 10 foot long, 0.25 inch wide column of 10% SE-30 on Chromosorb P was used. A colorless, volatile crystalline material (0.1525 g., 0.34 mmol) which sublimed at 108° was isolated. A 9.3% yield was obtained based on the initial hexamethylethane. Anal. C, 21.93; F, 78.06. Found: C, 21.94; F, 77.72. The $^{19}$F NMR consisted of a very strong singlet at −22.0 ppm. from an external trifluoroacetic acid reference. The gas-phase infrared spectrum contained bands at 1285(vs), 1260(vs), 1245(s), 1205(s), 1135(s), 880(w), 850(m), 735(m), 715(s), 535(vw), and 500(vw) cm$^{-1}$. The mass spectrum at 70 eV does not contain a parent peak but a strong P − 38+(P−F$_2$) peak is observed. The most intense peak in the spectrum is that of the CF$_3$$^+$ ion.

The major by-products of the fluorination of hexamethylethane are partially fluorinated species rather than fragments, and yields considerably higher than 10% could be achieved by recycling the products, by automating the process, or by using a longer cold reactor.

EXAMPLE 8

Cryogenic Zone Direct Fluorination of Norbornadiene

An apparatus as illustrated in FIG. 1 and as described in Example 1 was used.

The second zone of the cryogenic zone reactor was cooled to −78° C. with a dry ice slush. 5 ml. (0.049 moles) of norbornadiene was placed in a nickel boat in the reactant chamber. A helium flow of 60 cc./min. was initiated through the system to condense the norbornadiene in the first zone of the reactor, which was held to about −40° C. After 12 hours of flushing, the first zone was cooled to −78° C., the helium flow set at 30 cc./min., and a fluorine flow of 0.5 cc./min. started. Forty-eight hours later, zone 1 was warmed while zone 2 was maintained at −78° C. In this and other examples, it should be noted that when a particular zone is "allowed to warm" while a contiguous zone is cooled, the zone which is allowed to warm will reach an equilibrium temperature, not room temperature. For example, with the reactor used herein, if zone 2 is cooled to −78° C., zones 1 and 3 reach an equilibrium temperature when "allowed to warm" of approximately −40° C. Forty-eight hours later, the fluorine flow was increaded to 1.5 cc./min. Twenty-four hours after increasing the fluorine flow, zone 2 was warmed while zone 3 was held at −78° C. Twelve hours after zone 2 was warmed, the helium flow was reduced to 15 cc./min. Twelve hours after changing the helium flow, zone 4 was cooled and zone 3 allowed to warm. Twelve hours later, the helium flow was shut off. Twelve hours after cessation of helium flow, zone 4 was allowed to warm and the material was moved into a −78° C. glass trap under a pure fluorine flow. This fluorine flow of 1.5 cc./min. was maintained for four days. Then the fluorine was shut off and a 60 cc./min helium flow flushed through the system. The −78° C. trap was removed after 24 hours of flushing and taken to a vacuum line where the volatile material was condensed in a round bottomed flask. This material was then dissolved in carbon tetrachloride and the products were separated by cryogenic gas chromatography. The major products were perfluorobornane (1.261 g., $4.4 \times 10^{-3}$ moles, 8.22% yield) and monohydroundecafluoronorbornane (0.273 g., $9.29 \times 10^{-4}$ moles, 1.88% yield). Monohydroundeccafluoronorbornane can be represented by the following structure formula:

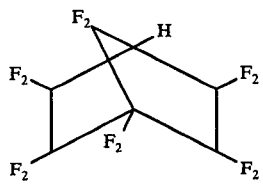

The two products were characterized by comparing their physical properties to those reported in the literature. See Campbell, S. F, Stephens, R. and Tatlow, J. C., Tetrahedron, 21, 2997 (1965); and, Homer, J. and Callaghon, D., J. Chem. Soc., 2471 (1969).

EXAMPLE 9

Cryogenic Zone Direct Fluorination of Norbornane

The apparatus of Example 1 was used.

1.045 g (.01087 moles) norbornane was introduced into the cryogenic zone reactor in a manner similar to norbornadiene in Example 8. Zone 1 was then cooled to −78° C., the helium flow set to 30 cc./min. and the fluorine flow to 0.55 cc./min. After 24 hours, zone 1 was allowed to warm and zone 2 was cooled to −78° C. Twenty-four hours later, the fluorine flow was increased to 1 cc./min. and after another 48 hours was increased to 1.5 cc./min. After 24 hours, zone 2 was warmed and zone 3 cooled to −78° C. Twelve hours later the helium flow was decreased to 15 cc./min. and 36 hours later was shut off. Twelve hours after shutting off the helium, zone 3 was warmed and zone 4 cooled to −78° C. Zone 4 was warmed 48 hours after it was cooled. The fluorine flow of 1.5 cc./min. was continued for four days, during which time the fluorinated material collected in a −78° C. glass trap. The system was then flushed for 24 hours by a 60 cc./min. helium flow. The products were worked up in the same way as the products from the norbornadiene reaction, and included perfluoronorbornane (0.414 g., $1.33 \times 10^{-3}$ moles, 12.22% yield) and monohydroundecafloronorbornane (0.260 g., $8.85 \times 10^{-4}$ mole, 8.14% yield).

EXAMPLE 10

Direct Fluorination of Bicyclo(2,2,2)octane

A cryogenic zone reactor as illustrated in FIG. 1 and as described in Example 1 was used.

0.683 ($6.19 \times 10^{-3}$ moles) of bicyclo(2,2,2)octane was introduced into the cryogenic zone reactor following the procedure of Example 8. Zone 1 was cooled and the fluorine flow set to 0.5 cc./min. with the helium flow at 60 cc./min. Thirty-six hours later, the helium flow was decreased to 30 cc./min. Twenty-four hours after that, the fluorine flow was increased to 10 cc./min. and zone 1 was warmed while zone 2 was cooled to −78° C. Twenty-four hours later, the helium flow was shut off and zone 4 was cooled as zone 3 was allowed to warm. Twenty-four hours later the fluorine flow was increased to 1.5 cc./min. Three hours after increasing the fluorine flow, zone 4 was allowed to warm and the material started to condense in a glass trap −78° C. The fluorine flow of 1.5 cc./min. was continued for five days. The product was worked up in the same fashion as that of Example 8. 0.5 g. ($1.37 \times 10^{-3}$ moles) perfluorobicyclo(2,2,2)octane was obtained (2.1% yield). It was characterized by comparing its properties to those described in Hollyhead, W. B., Stephans, R., Tatlow, J. C., and Westwood, W. T., Tetrahedron, 25, 1777 (1969).

EXAMPLE 11

Cryogenic Zone Direct Fluorination of Acetone

From the experimental data available, it is believed that perfluoroacetone could be prepared using a cryogenic zone reactor as described in Example 1 by the following method.

The first zone of a cryogenic zone reactor is cooled to −130° C. with a Union Carbide liquid nitrogen temperature controller. Acetone is introduced into the cold reactor using the procedure of Example 8. A helium flow of 42 cc./min. and a fluorine flow of 0.5 cc./min. is initiated. Thirteen hours later, zone 2 is cooled to −130° C. Four hours after this, the fluorine flow is increased to 1.0 cc./min. Thirty-two hours later, zone 3 is cooled to −130° C. (i.e., zone 2 is allowed to reach equilibrium). Sixteen hours after this, the helium flow is decreased to 25 cc./min. and the fluorine flow is increased to 1.5 cc./min. Twenty hours later, the helium flow is shut off. Five hours after this, zone 4 is cooled to −130° C. and 20 hours later, the fluorine is shut off. A helium flow of 60 cc./min. is started and zone 4 is allowed to warm up. The products can be trapped in a glass trap at −160° C. (isopentane slush bath) and worked up. Perfluoroacetone is a volatile liquid which is very hydroscopic. Its properties are described in Fwkuhara, N and Bigelow, L. A., J. Am. Chem. Soc., 63, 788 (1941).

EXAMPLE 12

Cryogenic Zone Direct Fluorination of Paraldehyde (a) With Four Zone Reactor Paraldehyde (1.90 g., .0144 moles) was syringed into a heated reactant chamber connected to a four zone cryogenic reactor. A flow of 160 cc./min. helium was passed through the chamber maintained at 50° C. and then into the cryogenic reactor with $Z_1$ at $-10°$ C. ($Z_2$, $Z_3$ and $Z_4$ were colder). After 12 hours, a flow of 0.5 cc./min. fluorine and 20 cc./min. helium was started after first cooling all zones to $-78°$ C. After 12 hours, the fluorine was increased to 1.0 cc./min. and zone 1 was allowed to rise to about $-40°$ C. Twelve hours after zone 1 reached equilibrium the second zone was allowed to warm to $-40°$ C., zone 1 then rose to $-20°$ C. The helium was then reduced to 10 cc./min. Twelve hours after zone 2 reached $-40°$ C. the fluorine was increased to 1.5 cc./min. and the third zone was allowed to rise to $-40°$ C., ($Z_2 = -20°$ C., $Z_1 = -10°$ C.). The helium flow was reduced to 5 cc./min. and 12 hours later stopped. After 12 hours, the fourth zone was allowed to warm subsequently allowing zones 1, 2 and 3 to reach room temperature. Finally as the reactor reached ambient temperature under a flow of pure fluorine, the product passed through a sodium fluoride charged hydrogen fluoride trap and collected in a $-196°$ C. trap. The reactor was flushed with helium for several hours and the glass trap removed and its contents fractionated by vacuum distillation.

Further purification by gas-liquid chromatography using a fluorosilicone (QF1-0065, 13% on chromosorb P) column resulted in the isolation and characterization of the following compounds: (Bis pentafluoroethyl ether, perfluoro(ethyl acetate), perfluoro-1,2-diethoxyethane, α-hydrotetrafluoroethyl trifluoroacetate, α-hydrotetrafluoroethylpentafluoroethyl ether, trifluoroacetyl fluoride and pentafluoroethoxy carbonyl fluoride.

(b) With Six Zone Reactor

A second reaction using a more gradual fluorination procedure on a six zone cryogenic reactor produced four completely fluorinated major products which were: perfluoroparaldehyde, perfluoro-1,2-diethoxyethane, and two products tentatively identified as

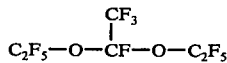

and $C_2F_5-O-CF_2-O-C_2F_5$.

The six zone cryogenic reactor procedure is as follows. Paraldehyde (1.80 g., 0.0137 moles) was syringed into the reactant chamber connected to the inlet of the six zone cryogenic reactor. The evaporation was heated to 50° C. and a 160 cc./min. flow of helium carried the paraldehyde into the reactor with $Z_1$ cooled at 0° to $-4°$ C. ($Z_1 = -12$, $Z_3 = -30$, $Z_4 = -54$, $Z_5$ and $Z_6 = -78°$ C.). After 12 hours, a flow of 0.5 cc./min. fluorine and 20 cc./min. helium was initiated and zones 1-6 were cooled to $-78°$ C. After 24 hours, zone 1 warmed to $-50°$ C. After an additional 24 hours, zone 2 warmed to $-40°$ C. ($Z_1 = -30°$ C.). Twelve hours later the fluorine was increased to 1.0 cc./min. Twelve hours later zone 3 warmed to $-50°$ C. ($Z_2 = -30°$ C., $Z_1 = -15°$ C.). Twelve hours later the fluorine was increased to 1.5 cc./min. After an additional 12 hours, the helium flow was reduced to 10 cc./min. and zone 4 was warmed to $-50°$ C. ($Z_3 = -30°$ C., $Z_2 = -15°$ C., $Z_1 = =4°$ C.). Twenty-four hours later the helium as reduced to 5 cc./min. and 12 hours later $Z_5$ was warmed to $-55°$ C. ($Z_4 = -30°$ C., $Z_5 = -15°$ C., $Z_2 = -2°$ C., $Z_1 = +4°$ C.). Twenty-four hours later the helium flow was stopped and zone 6 was changed from dry ice control at $-78°$ C. to a Cryogenic Controls Corp. Model 000-123 temperature controller at $=80°$ C. Twelve hours later the temperature of zone 6 was reduced to $-40°$ C. and on subsequent 12-hour periods reduced to $-20°$ C., 0° C. and then room temperature (about $+30°$ C.). As the reactor warmed, the product passed through a hydrogen fluoride trap filled with sodium fluoride pellets into a glass trap at $-196°$ C. After flushing the reactor with helium for several hours, the contents of the glass trap were removed and fractionated to remove $CF_4$, $C_2F_6$ and $COF_2$ (50% by volume) and the remainder was purified by gas-liquid chromatography and characterized by infrared, mass spectrometry and by $^{19}F$ NMR.

EXAMPLE 13

Cryogenic Zone Direct Fluorination of Morpholine To Perfluoro-N-Fluoromorpholine .76 g. of morpholine ($C_4H_9NO$) were admitted to a four zone cryogenic reactor. A helium flow of 20 cc./min. and a fluorine flow of 1 cc./min. was initiated after the reactor had been purged with helium. After one day, the helium was reduced to 10 cc./min. and the first zone ($-78°$ C.) was warmed. The second day the second zone was warmed to room temperature and the third was cooled. On the fourth day, the fourth zone was cooled to $-78°$ C. and the third zone was warmed to 20° C. On the fifth day, the fluorine flow was terminated and the products were collected in a glass trap.

The volatile products from the reactor were separated on an SE-30 glc column. The infrared spectrum of perfluoro-N-fluoromorpholine: (cm$^{-1}$, intensity, possible assignments) 1371(w), 1338(m), 1291(s), $CF_2$ stretch, 1233, shoulder on 1217, 1217(vs), $CF_2$ stretch, 1146 and 1124 (s), doublet, COC cym. stretch ?, 967(m), NF stretch, 922(m) NF stretch, 688(m), 661(w), 606(mb); (w, weak; m, medium; s, strong; vs., very strong; mb, medium and broad). The NF stretch has been previously reported as 922 and 975 cm$^{-1}$. The mass spectrum of $C_4F_9NO$ with the major m/e, intensity relative to m/e = 114, and possible ions was: 250, 0.1, $^{13}CC_3F_9NO+$, $C_4F_9{}^{15}NO+$(cal 0.07); 249, 15, $C_4F_9NO+$(parent); 231, 0.3 isotopes of 230 (cal 0.2); 230, 4.0, $C_4F_8NO+$; 202, 1.7, $C_3F_8N+$; 185, 1.0, $C_3F_7O+$; 180, 2.2, $C_3F_6NO+$; 169, 1.4, $C_3F_7+$; 165, 1.7, isotopes of 164 (cal. 1.4); 164, 40.3, $C_3F_6N+$; 152, 1.7, $C_2F_6N+$; 151, 1.1; 146, 0.8, isotopes of 145 (cal 0.7); 145, 17.7, $C_3F_5N+$; 142, 1.7, $C_3F_4NO+$; 120, 1.8, $^{13}CCF_5+$ (cal 1.6); 119, 74.6, $C_2F_5+$; 115, 3.0, isotopes of 114 (cal. 2.5); 114, 100.0, $C_2F_4N+$; 101, 5.3; 100, 38.8, $C_2F_4+$; 97, 8.0, $C_2F_3O+$; 95, 9.4, $C_2F_3N+$; 92, 3.2, $C_2F_2NO+$; 81, 1.3, $C_2F_3+$, $C_4FN+$; 76, 4.6, $C_2F_2N+$; 76, 1.3 ; 69, 52.3, $CF_3+$; 51, 3.3 ; 50, 10.0, $CF_2+$; 47, 6.6, $CFO+$; 44, 47.0, $CO_2+$; 43, 6.6, $C_2F+$; 31, 3.3, $CF+$; and the usual peaks under m/e = 30. In addition, two metastables were apparent at 79.17 and 41.76 m/e. These represent the neutral fragments of fluorine and FCN leaving the m/e = 114, $C_2F_4N+$, to yield m/e = 95, $C_2F_3N+$, and m/e = 69, $CF_3+$, respectively.

The 19-F nuclear magnetic resonance spectrum was measured on the neat perfluoro-N-fluoromorpholine with an external reference to trifluoroacetic acid. The chemical shifts and the integration were in agreement with the previously reported values. Yields comparable to the electrochemical fluorination of morpholine were easily attained (8%).

Another component of the reaction has been identified as bispentafluoroethyl ether on the basis of its infrared spectrum which was identical in all aspects to the published spectrum, and its mass spectrum. The major m/e intensities, and possible ions were: 235, 1, $CF_2CF_2OC_2F_5^+$; 185, 189, $C_3F_7O^+$; 135, 6, $C_2F_5O^+$; 120, 168; 119, offscale, $C_2F_5^+$; 116, 10, $C_2F_4O^+$; 100, 26, $C_2F_4^+$; 92, 78; 70, 33 : 69, offscale, $CF_3^+$; 66, 6, $COF_2^+$; 50, 61, $CF_2^+$; 47, 60, $COF^+$; 45, 10 ; 44, 621, $CO_2^+$; 43, 92, $C_2F^+$; 31, 143, $CF^+$; and the usual peaks under 30. Also, identified by infrared and mass spectra has been hexafluoroethane, pentafluoroethyldifluoroamine, and nitrogen trifluoride. Tentatively identified was $CF_3OCF_2CF_2N(F)CF_3$. This last compound was in small amount and represents β-cleavage of morpholine ring. The nitrogen elimination from the morpholine ring represents the major side reaction and adds to the evidence of the weakness of the carbon-nitrogen bond compared to the carbon-oxygen and carbon-carbon bonds.

EXAMPLE 14

Direct Fluorination of diglycolic Anhydride

Combined vertical and horizontal cryogenic zone reactors were used. The vertical reactor was as illustrated in FIG. 3 except that it had only two independently controllable temperature zones, an upper zone and a lower zone. It was formed from a nickel reactor column having a 1.0 inches I.D. and packed with fluorinated copper packing. Fluorine and helium were introduced through ¼ inch copper tubing; the exit was connected by ¼ inch copper tubing to the inlet of a horizontal cryogenic zone reactor as described in Example 1. The upper zone of the vertical reactor was loosely packed with copper turnings, whereas the lower zone was packed with copper cuttings. An HF trap, filled with sodium fluoride pellets, was placed on the exit tubing of the horizontal reactor, as well as a liquid nitrogen U-shaped product trap.

Diglycolic anhydride (1.0 g., 8.64 mmol., 250 mesh) was distributed evenly over the top of the loosely packed copper turnings in the upper zone of the vertical reactor. The reactor was closed, and the upper zone was cooled to −20° C. with a Freon temperature controller whereas the lower zone was cooled to 0° C.

A flow of 0.5 cc./min. fluorine and 40.0 cc./min. helium was started. As the volatile products left the vertical reactor, they were condensed in the four-zone cryogenic reactor whose respective zones were cooled to −40° C., −78° C., −78° C., −78° C. After four days, the upper zone of the vertical reactor was warmed to 0° C. and the lower zone to room temperature. The helium flow was reduced to 20 cc./min. The following day the upper zone was warmed to room temperature. After 24 hours, the helium flow was reduced to 10 cc./min. and zone 2 of the horizontal reactor was allowed to warm to its equilibrium temperature.

Twenty-four hours later the helium was shut off and zone 3 was allowed to warm to equilibrium. Twenty-four hours later zone 4 was warmed and the helium flow was raised to 20 cc./min. After 24 hours, the fluorine was shut off, the system flushed with helium and the glass collector trap sealed and removed from the system.

The products collected were vacuum distilled through −78° C., −131° C. and −196° C. traps. The contents of the −196°C. trap were discarded. The contents of the −78° C. and −131° C. traps were combined and hydrolyzed in 2.0 molar potassium hydroxide solution. The solution was acidified with concentrated sulfuric acid, extracted five times with ethyl ether, dried over a Linde 4A molecular sieve and the ether evaporated. The oily residue remaining was fractionated through −78° C. and −196° C. traps.

The residue from the fractionation was sublimed yielding approximately 60 mg. (3.3%) of perfluorodiglycolic acid. Approximately 200 mg. of additional material was collected in the −78° C. trap which contains at least two other ether acid fragments of the parent compound.

Perfluorodiglycolic acid is a waxy solid (m.p. 77°-79° C.). Its $^{19}F$ NMR consists of a sharp singlet at +78.3 ppm. relative to internal $CFCl_3$ in a diethyl ether/carbon tetrachloride solution. The carbonyl stretching frequency in the infrared is 1773 cm.$^{-1}$ At least two other new products were also isolated. The first new product has been identified as bis(-monohydrodifluoromethyl)ether, $HCF_2$-O-$CF_2H$(b.p. −1°). This ether is a malodorous, somewhat moisture sensitive gas which has been characterized by $^{19}F$ and $^1H$ NMR, infrared, mass spectrometry and by molecular weight (120 cf. 118). The yield of this product is approximately 17%.

The remaining fraction (5 − 10%) was found to contain the —O—CHF—C(O)F group and may be O[CHF—C(O)F]$_2$ the molecular weight of the gas chromatograph purified substance is approximately 180 which is not inconsistent with the diacyl fluoride which is 174, especially since minor hydrolysis can cause molecular associations and raise the molecular weight. The $^{19}F$ NMR is somewhat more complex than would be predicted on the basis of the acyl fluoride structure and leads to some doubt as to whether there is a mixture present or whether the complement of the —O—CHF—C(O)F group is different.

The raw data from the mass spectra for $HCF_2$—O—$CF_2H$ were:

| m/e | Hi(1.75) | Lo(1.0) | Identity |
|---|---|---|---|
| 30 | 14 | | |
| 31 | 22.5×9 | 11 | CF |
| 32 | 17×9 | 8 | $O_2$,CFH |
| 36 | 9.5 | | |
| 47 | 143 | 7.9 | CFO |
| 48 | 93.5×3 | 15.6 | |
| 49 | 33.5 | | |
| 50 | 133.5 | 7.0 | |
| 51 | off scale | 150 (44×3) (15×9) | $CHF_2$ |
| 52 | 32.8 | | |
| 66 | 17.5 | | |
| 67 | 19.0 | | |
| 69 | 29 | | $CF_3$ |
| 71 | 39.5 | | |
| 79 | 22.3 | | $C_2OF_2H, HCF_2-\overset{\overset{O}{\|}}{C}$ |
| 85 | 8 | | |
| 98 | 62.4 | 3 | $C_2F_3OH\ HCF_2-\overset{\overset{O}{\|}}{C}-F$ |
| 101 | 23.2 | | $C_2F_4H\ HCF_2-CF_2$ |
| 116 | 21.8 | | $C_2F_4O\ CF_2\overset{O}{\underset{}{\diagup\diagdown}}CF_2$, |

-continued

| m/e | Hi(1.75) | Lo(1.0) | Identity |
|---|---|---|---|
|  |  |  | $CF_3-\overset{\overset{O}{\|}}{C}-F$ |
| 117 | 81 | 4 | $C_2F_4OH$  $HCF_2-O-CF_2$ |

Its $^{19}F$ and proton NMR were:

| $^{19}F\ \phi = +88.69$ ppm. | J = 69.0 | doublet* |
|---|---|---|
| $^1H\ \alpha = -5.997$ ppm. | J = 70.9 | triplet** |

*Due to "configurational isomers" the doublet is partially split into triplets (J = 1.9 hz) or doublets (J = 3.8 hz).
**The triplet is partially split into a possible pentet (J = 3.8 hz).

EXAMPLE 15

Cryogenic Zone Direct Fluorination of Benzoyl Chloride To Produce Perfluorocyclohexanoic Acid The apparatus and procedure of Example 1 were used.

0.59 g. of benzoyl chloride was transferred into the cooled ($-78°$ C.) first zone of the reactor. After purging with helium, the helium flow was set at 20 cc./min. and the fluorine flow was set at .5 cc./min. On the second day, the helium flow was reduced to 10 cc./min. On the third day, the helium flow was terminated and the first trap was warmed as the second trap was cooled to $-78°$ C. On the fourth day, the third trap was cooled and the second trap was warmed. On the fifth day, the fourth trap was cooled and the third warmed. On the fifth day, the reactor was purged with helium and the fourth was warmed. The products were collected in a glass trap.

Fractional distillation of the collected products on the vacuum line yielded material which had three distinct volatilites. A $-196°$ trap (liq. nitrogen) contained some carbonyl fluoride and silicon tetrafluoride as identified by their infrared spectrum. A $-78°$ trap (Dry Ice-trichloroethylene) contained a liquid which when further purified on a glc column of 13% Fluorosilicone QF-1 (FS1265) Oil proved to hold the materials of interest. The infrared spectrum of perfluorocyclohexylcarbonyl (gas at 6 torr) in wavenumbers, intensity and syggested assignments: 1886(s), carbonyl stretch, 1375(w), 1318(s), 1250(b-vs) CF stretch, 1200(vs), CF stretch, 1187, shoulder on 1200, 1170, shoulder on 1200, 1120(m), 1110 shoulder on 1120, 1068(w), 1028(s), 980(vs), 940(m), 895(m), 877(m), 858(w), 834(w), 734 shoulder on 717, 717(m), 673(vw), 641(m). 541(vw), 509(w), 469(vw), where vw, very weak; w, weak; m, medium; s, strong; vs, very strong; b, broad. The bands at 980, 1200, 1250, and 1318 cm$^{-1}$ have been reported to be characteristic of perfluorocyclohexyl compounds. See Thompson, H. W. and Temple, R. B.; J. Chem. Soc., 1432 (1948). A mass spectrum of this material supports the formulation of $C_6F_{11}C(O)F$. The major m/e, intensities relative to m/e, of 131, and the possible ions were: 328, 0.7, $C_7F_{12}O+$ (parent); 309, 1.1, $C_7F_{11}$ $O^+$; 281, 2.2, $C_6F_n^+$; 263, 1.6; 262, 5.6, $C_6F_{10}^+$; 259, 1.1, $C_6F_9O^+$; 247, 0.9, $C_5F_9O^+$; 243, 5.3, $C_6F_9^+$; 231, 6.4, $C_5F_9O^+$; 213, 5.3, $C_4F_7O_2^+$; 212, 1.3, $C_5F_8^+$; 209, 1.6, $C_5F_7O^+$; 197, 2.7, $C_4F_7O^+$; 193, 4.0, $C_5F_7^+$; 190, 0.9, $C_5F_6O^+$; 185, 1.3, $C_3F_7O^+$; 182, 1.3; 181, 20.0, $C_4F_7^+$; 178, 1.1, $C_4F_6O^+$; 175, 4.7, $C_4F_5O_2^+$; 169, 3.6, $C_3F_7^+$; 163, 9.3, $C_3F_5O_2^+$; 162, 11.1, $C_4F_6^+$; 160, 2.7; 159, 34.0, $C_4F_5O^+$; 155, 1.1, $C_5F_5^+$; 151, 3.1, $C_2F_5O_2^+$; 150, 2.9, $C_3F_6^+$; 149, 4.4, $c_5F_3O_2^+$; 147, 12.9, $C_3F_5O^+$; 145, 0.9; 144, 6.2, $C_3F_4O_2^+$; 143. 3.1, $C_4F_5^+$; 141, 7.8, $C_7F_3^+$; 135, 2.9, $C_2F_5O^+$; 132, 5.6; 131, 100., $C_3F_5^+$; 129, 2.2, $C_6F_3^+$; 128, 3.3, $C_3F_4O^+$; 119, 17.8, $C_2F_5^+$; 116, 3.1, $C_2F_4O^+$; 114, 1.6, $C_5F_2O^+$; 113, 40.0, $C_2F_3O_2^+$; 112, 1.8, $C_3F_4^+$; 110, 6.7, $C_6F_2^+$; 101, 2.0; 100, 31,0, $C_2F_4^+$; 95, 2.0, $C_5FO^+$; 93, 3.6, $C_3F_3^+$; 91, 1.8; 87, 3.8, $C_3FO_2^+$; 86, 1.6; 85, 33.3, $SiF_3^+$; 82, 7.6, $C_2F_2O_2^+$; 75, 2.4, $C_2FO_2^+$; 70, 1.1; 69, 80.0, $CF_3^+$; 51, 17, 1, $CF_2H^+$; 87, 37.4, $SiF_+$; 40, 15.1, $C_2O^+$; plus the usual peaks under $^m/e = 40$. Some of the prominent fragments have been assigned with two oxygens instead of the expected one. The water content of the inlet system appears to have been quite high (37.8 relative intensity) and the perfluorocyclohexylcarbonyl fluoride had probably hydrolyzed to perfluorocyclohexylcarboxylic acid, $C_6F_{11}C(O)OH$. The 19-F nmr of perfluorocyclohexylcarbonyl fluoride as a neat liquid at 35° with external reference of Freon-11 (in ppm; minus is downfield from $CCl_3F$); $-35.9$, the carbonyl fluoride; 117.3, 122.7, 127.5, 129.5, 131.0, 136.3, 139.3, 141.8, 144.5, 147.3, 167.8, and 181.9. The fine structure was not resolvable. The yield of acid fluoride exceeded 15%.

Also, isolated and identified in the $-78°$ trap by infrared, mass and $^{19}F$ NMR spectrocopies has been perfluorocyclohexane. The yield of this compound varies with the fluorination conditions but has been generally around 10%. With high fluorine flow for initial fluorination conditions a 10% yield of chloroundecaflourocyclohexane was isolated. The compound was confirmed by infrared, mass and $^{19}F$ NMR spectroscopies. The yield of cloroundecafluorocyclohexane was reduced to under 1% by low initial fluorine flow. The least volatile fraction, $-41°$ trap, (acetonitrile slush) contained, based on infrared spectra, carbonyl, fluorine and hydrogen stretches which suggested a partially fluorinated cyclohexylcarbonyl fluoride. Extended fluorination reduced this material but did not eliminate it.

EXAMPLE 16

Cryogenic Zone Direct Fluorination of Glutaronitrile

A four zone reactor packed and pretreated as previously described and connected to a glass trap maintained at $-78°$ C. was used in the fluorination of glutaronitrile.

In a representative run 2 cc. (1.98 g.) of glutaronitrile, previously dried over $CaH_2$, was injected into the coil of the copper tubing just ahead of the reactor and was carried in the cold reactor under a high flow (40 cc./min.) of helium while keeping the second zone of the reactor at $-78°$ C. using a dry ice-isopropanol slush. After three hours, the first zone of the reactor was also cooled down to $-78°$ C. and the fluorine flow was initiated. The fluorination was carried out as follows:

| Stage | He Flow (cc./min.) | $F_2$ Flow (cc./min.) | Time Period(hrs) | Reactor Temp. |
|---|---|---|---|---|
| 1 | 40 | 0.5 | 24 | 1&2 zone-78° C. |
| 2 | 40 | 1.0 | 24 | 1&2 " " |
| 3 | 40 | 1.5 | 24 | 2&3 " " |
| 4 | 40 | 2.0 | 24 | 2&3 " " |
| 5 | 20 | 2.0 | 24 | 3&4 " " |
| 6 | 10 | 2.0 | 12 | 4 zone -78° C. |
| 7 | — | 2.0 | 12 | warming to RT |

At the end of this period the fluorine was shut off and the system was flushed with helium. The glass trap containing the products was then disconnected from the fluorination set-up and the contents were transferred onto a conventional vacuum line. The products were fractionated using a series of three traps at temperatures −196° C. (liquid N$_2$), −95° C. (toluene slush) and −63° C. (chloroform slush). The most volatile fraction contained almost exclusively SiF$_4$ and the least volatile fraction contained partially fluorinated species. The −95° C. fraction was further separated on the gas chromatograph, using a 10 foot Fluorosilicon column (QF-1-0065) yielding the compounds n-n-C$_5$F$_{12}$, C$_5$F$_{11}$NF$_2$ and NF$_2$(CF$_2$)$_5$NF$_2$ in that order.

Separation of the reaction products on the gas chromatograph yielded three fluorocarbons which have been identified to be n-C$_5$F$_{12}$, CF$_3$(CF$_2$)$_4$NF$_2$ and F$_2$N(CF$_2$)$_5$NF$_2$. The last of these is new. These compounds were identified as follows:

1. Perfluoropentane, n-C$_5$F$_{12}$

This compound was identified by means of its infrared spectrum which was identical with the one published in the literature.

2. 1-Azaperfluorohexane, CF$_3$(CF$_2$)$_4$NF$_2$

This N-fluoroamine was identified on the basis of its infrared, nmr and mass spectra. The infrared spectrum of this compound resembled that of n-C$_5$F$_{12}$ and in addition contained a doublet between 1000 and 900 cm$^{-1}$ which was attributed to the NF$_2$ group. The nmr spectrum of CF$_3$C$^\delta$F$_2$C$^\gamma$F$_2$C$^\beta$F$_2$C$^{\alpha F_2}$NF$_2$ exhibited five peaks at − 14.1 (NF$_2$), 117.1 ($\alpha$), 124.0 ($\beta$ and $\gamma$) 128.0 ($\delta$) and 83.5 (CF$_3$) ppm with respect to CFCl$_3$ in the ratio of 1:1:2:1:1, which was in agreement with the spectrum reported by Bigelow and co-workers. The fluorines of the $\beta$ and $\gamma$ groups were not resolved. The mass spectrum of the compound contained highest peaks at m/e 302, C$_5$F$_{12}$N (parent minus F) and 269, C$_5$F$_{11}$ (parent minus NF$_2$) as well as many other expected peaks.

3. 1,7-Diazaperfluoroheptane F$_2$N(CF$_2$)$_5$NF$_2$

This new compound was identified on the basis of its infrared, nmr and mass spectra. The infrared spectrum showed considerable similarity to that of n-C$_5$F$_{12}$ and contained the characteristic doublet between 1000 and 900 cm$^{-1}$, although it has been transformed now into a sharp peak and a shoulder due probably to the highest symmetry of the compound. The nmr spectrum of F$_2$NC$^\alpha$F$_2$C$^\beta$F$_2$C$^\gamma$F$_2$CF$_2$CF$_2$NF$_2$ exhibited three peaks at − 13.5 (NF$_2$), 116.3 ($\alpha$) and 122.6 ($\beta$ and $\gamma$) ppm with respect to CFCl$_3$ in the ratio 2:2:3. As expected the fluorines on the $\beta$ and $\gamma$ CF$_2$ groups were not resolved. The mass spectrum of the compound contained highest peaks at m/e 335, C$_5$F$_{13}$N$_2$ (parent minus F), 302 C$_5$F$_{12}$N (parent minus NF$_2$) and a pronounced peak at 250 C$_5$F$_{10}$ as well as many others as expected.

The yield 1,7-diazaperfluoroheptane was about 3%. Part of the difficulty lies in the fact that replacement of the last hydrogen atoms on the carbon chain becomes increasingly difficult due to steric difficulties with the larger fluorine atoms. Nevertheless it is worth noticing that direct fluorination of perfluoroglutaronitrile NC(CF$_2$)$_3$CN by Bigelow's method yielded only C$_5$F$_{11}$NF$_2$ and CF$_2$CF$_2$CF$_2$CF$_2$NF.

EXAMPLE 17

Direct Fluorination of the Acid Chloride of Acetic Acid to Yield Trifluoror Acetyl Fluoride: A Route to Trifluoroacetic Acid 2.12 g. of CH$_3$COCl was condensed onto the cooled first zone of an eight zone cryogenic reactor. A 20 cc./min. flow of helium was started after purging and a 0.5 cc./min. fluorine flow was begun. The following warm-up procedure was used.

| | | |
|---|---|---|
| 24 hrs. | first zone warmed | second cooled to −78° C. |
| 48 hrs. | second zone warmed | third cooled to −78° C. |
| 72 hrs. | third zone warmed | fourth cooled to −78° C. |
| 96 hrs. | fourth zone warmed | fifth cooled to −78° C. |
| 110 hrs. | fifth zone warmed | sixth cooled to −78° C. |
| 134 hrs. | sixth zone warmed | seventh cooled to −78° C. |
| 158 hrs. | seventh zone warmed | eighth cooled to −78° C. |

After 182 hours, the fluorine flow was terminated and the products were collected in a glass trap. The products were then hydrolyzed with H$_2$O.

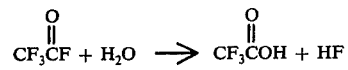

1.5 g. of trifluoroacetic acid was obtained by separation on a glc. column. It was characterized by an appropriate singlet in the NMR, a mass spectra which revealed a parent at 39 (CF$_3$COOH$^+$); CF$_3$CO$^+$, 33, and CF$_2$COOH$^+$ 32 plus other appropriate fragments. The infrared spectra was also taken and was identical with the well known trifluoroacetic acid spectrum. Characterization was also confirmed by boiling point and molecular weight.

EXAMPLE 18

Direct Fluorination of Adamantane

A reactor as illustrated in FIG. 1 was used except that it had only one cold zone which was provided by placing an ice bucket around the reactor, approximately at its center.

A glass trap was attached to the end of the system which was flushed with a 60 cc./min. flow of helium for four hours. The ice bucket was filled with a −78° C. bath (dry ice and isopropyl alcohol) and allowed to cool. 0.72300 g. (5.307 m moles) of adamantane was placed in a boat and then in the reactor so it was in the middle of the area cooled by the −78° C. bath. The helium flow was set at 60 cc./min. and the fluorine to 0.5 cc./min. for 31 hours. Then the helium was lowered to 30 cc./min. and the fluorination continued for 24 hours. The fluorine was then raised to 1.0 cc./min. and the system (still at −78° C.) left for 31 hours. The helium was lowered to 15 cc./min. and after 24 hours, the fluorine flow raised to 1.5 cc./min. The fluorination at 15 cc./min. helium and 1.5 cc./min. fluorine was continued for 50 hours. Then the helium flow was shut off and pure fluorine (1.5 cc./min.) was used for 20 hours. The −78° C. bath was then scooped out and replaced with ice water. The fluorination with pure fluorine was continued at 0° for 30 hours. The ice-bath was removed and the fluorination at room temperature continued for 84 hours. The fluorine flow was then increased to 2 cc./min. and the system left for 5 days. The glass trap (which has been cooled to −78° C. at the beginning of the run) was removed and taken to the vacuum line after the entire system had been flushed with a 60 cc./min. helium flow for two days. The material was condensed into a 5 ml. pear-shaped flask, dissolved with toluene and CFCl$_3$ and separated on the gas chromatograph. 0.09465 g. (2.33×10$^{-4}$ moles) of monohydropentadecafluoroadamantane was obtained (4.4% yield).

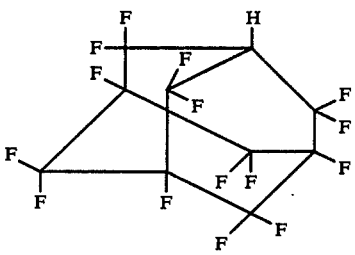

Perfluoroneopentane is obtained by refluorination of the monohydroperfluoroadamantane with 1 cc./min. fluorine flow for two days at −60° C.

Monohydropentadecafluoroadamantane has not been previously prepared. It exhibits a mass spectrum consisting of the following peaks m/e 406 ($C_{10}F_{15}H^+$), 405 ($C_{10}F_{15}^+$), 205 ($C_6F_7^+$), 131 ($C_3F_3^+$), 69 ($CF_3^+$). Its melting point (sealed capillary) was 225°–226° C. Its gas phase infrared spectrum consisted of bands at 2911(vw), 1305(sh), 1285(vs), 1080(m), 970(s), 745(m), 655(w) cm$^{-1}$. The $^{19}F$ NMR, taken in a solution of $CCl_4$ and $CFCl_3$, consisted of a quintet at 121.5 ppm. upfield from $CFCl_3$ and a broad unresolved peak at 223.6 ppm. upfield from $CFCl_3$. The proton NMR showed a broad peak at 1.75 ppm. downfield from TMS. Analytical results. Calc. $C_{10}F_{15}H$, % C 29.575 % H 0.248%, % F 70.176. Found % C 29.69, % H 0.49, % F 70.16.

What is claimed is:

1. A direct fluorination apparatus comprising, in combination:
   a. a reactor having a reactant inlet at one end of said reactor and a product outlet at the opposite end of said reactor;
   b. means for separating said reactor into a plurality of independently controllable temperature zones positioned consecutively within said reactor between the reactant inlet and the product outlet;
   c. means for introducing a source of first reactant at said reactant inlet, said first reactant being a source of elemental fluorine;
   d. means for introducing a second gaseous reactant to be fluorinated into said reactor at said reactant inlet; and,
   e. means for cooling each of said independently controllable temperature zones to a temperature in the range from about −190° C to about +20° C, said temperature being sufficiently low in each zone to cause partially fluorinated second reactant to condense therein as it passes therethrough whereby further fluorination of said second reactant takes place.

2. An apparatus of claim 1 wherein said means for introducing a source of elemental fluorine comprise means for introducing fluorine gas.

3. An apparatus of claim 2 wherein said means for introducing fluorine gas includes means for introducing an inert gas simultaneously thereby forming a mixture of fluorine gas and the inert gas, and means for controlling the concentration of fluorine gas in said mixture so that a low concentration can be introduced to said reactor and an increasing concentration can be provided as fluorination proceeds within the reactor.

4. An apparatus of claim 3 wherein said reactor comprises a column containing metal packings.

5. An apparatus of claim 4 wherein said means for separating comprise thermal insulating means.

6. An apparatus of claim 5 wherein said column packings comprise copper packings.

7. An apparatus of claim 6 wherein said reactor is formed from a material which is inert to elemental fluorine.

8. An apparatus of claim 7 wherein said means for introducing an inert gas comprises means for introducing nitrogen or helium.

9. An apparatus of claim 8 wherein said means for cooling comprise liquid nitrogen temperature control elements.

10. An apparatus of claim 8 wherein said means for cooling comprise Freon temperature control elements.

11. An apparatus of claim 1 also including means for heating said zones to a temperature above the boiling point of said reactant to be fluorinated.

12. An apparatus of claim 5 also including means for heating said zones to a temperature above the boiling point of said reactant to be fluorinated.

13. An apparatus for fluorinating a reactant by contacting it with elemental fluorine comprising, in combination:
   a. a column reactor having a reactant inlet and a product outlet, said column reactor being packed with a suitable fluorination packing;
   b. thermal insulating means for dividing said column reactor into a plurality of independently controllable temperature zones;
   c. temperature control means for lowering the temperature of each of said zones to a temperature below the freezing point of said reactant, said temperature being in the range of from about −190° C to about +20° C; and,
   d. means for introducing a mixture of elemental fluorine gas and an inert gas into said reactor, said means including metering means for introducing initially a mixture having a low concentration of fluorine gas while subsequently increasing the concentration of fluorine as fluorination of said reactant proceeds within said reactor.

14. A reactor of claim 13 wherein said thermal insulating means divides said column reactor into at least four independently controllable temperature zones.

* * * * *